US011785923B2

(12) United States Patent
Shultz et al.

(10) Patent No.: US 11,785,923 B2
(45) Date of Patent: Oct. 17, 2023

(54) GENETICALLY MODIFIED NON-HUMAN ANIMALS AND METHODS RELATING TO COMPLEMENT DEPENDENT CYTOTOXICITY

(71) Applicants: The Jackson Laboratory, Bar Harbor, ME (US); University of Massachusetts, Boston, MA (US)

(72) Inventors: Leonard D. Shultz, Bar Harbor, ME (US); Mohit Kumar Verma, Bar Harbor, ME (US); Dale L. Greiner, Hubbardston, MA (US); Michael A. Brehm, Dudley, MA (US)

(73) Assignees: The Jackson Laboratory, Bar Harbor, ME (US); University of Massachusetts, Boston, MA (US)

( * ) Notice: Subject to any disclaimer, the term of this patent is extended or adjusted under 35 U.S.C. 154(b) by 700 days.

(21) Appl. No.: 16/886,289

(22) Filed: May 28, 2020

(65) Prior Publication Data
US 2020/0359609 A1    Nov. 19, 2020

Related U.S. Application Data

(63) Continuation of application No. 15/736,951, filed as application No. PCT/US2016/037882 on Jun. 16, 2016, now Pat. No. 10,701,911.

(60) Provisional application No. 62/326,958, filed on Apr. 25, 2016, provisional application No. 62/180,369, filed on Jun. 16, 2015.

(51) Int. Cl.
*A01K 67/027* (2006.01)
*C12N 15/90* (2006.01)
*C07K 14/47* (2006.01)
*A61K 49/00* (2006.01)

(52) U.S. Cl.
CPC ........ *A01K 67/0275* (2013.01); *A01K 67/027* (2013.01); *A01K 67/0271* (2013.01); *A61K 49/0008* (2013.01); *C07K 14/472* (2013.01); *C12N 15/907* (2013.01); *A01K 2207/12* (2013.01); *A01K 2207/15* (2013.01); *A01K 2217/07* (2013.01); *A01K 2227/105* (2013.01); *A01K 2267/0387* (2013.01)

(58) Field of Classification Search
None
See application file for complete search history.

(56) References Cited

U.S. PATENT DOCUMENTS

| 9,546,384 | B2 | 1/2017 | Frendewey et al. |
| 10,701,911 | B2 | 7/2020 | Shultz et al. |
| 2005/0249666 | A1 | 11/2005 | Nakamura et al. |
| 2015/0159175 | A1 | 6/2015 | Frendewey et al. |

FOREIGN PATENT DOCUMENTS

| CN | 102821600 A | 12/2012 |
| JP | 2007-527216 A | 9/2007 |
| JP | 2008-514205 A | 5/2008 |
| WO | WO 2005/013682 A2 | 2/2005 |
| WO | WO 2006/039678 A2 | 4/2006 |
| WO | WO 2011/078301 A1 | 6/2011 |

OTHER PUBLICATIONS

EP 16812441.0, Jan. 17, 2019, Extended European Search Report.
PCT/US2016/037882, Sep. 14, 2016, International Search Report and Written Opinion.
PCT/US2016/037882, Dec. 19, 2017, International Preliminary Report on Patentability.
Carney et al., Structural aspects of the human C5 gene. Intron/exon organization, 5'-flanking region features, and characterization of two truncated cDNA clones. J Biol Chem. Oct. 5, 1991;266(28):18786-91.
Lu et al., Research and application progress of humanized mouse model. Medical Recapitulate. Sep. 2014;20(18):3281-4. doi: 10.3969/j.issn.1006-2084.2014.18.007.
Extended European Search Report dated Jan. 17, 2019 in connection with Application No. EP 16812441.0.
International Search Report and Written Opinion dated Sep. 14, 2016 in connection with Application No. PCT/US2016/037882.
International Preliminary Report on Patentability dated Dec. 19, 2017 in connection with Application No. PCT/US2016/037882.
[No Author Listed] Immunodeficient mice: the NOD connection. The Jackson Laboratory. Feb. 1, 2014. 4 pages. Retrieved from the internet <https://www.jax.org/news-and-insights/jax-blog/2014/february/immunodeficient-mice-the-nod-connection>.

(Continued)

*Primary Examiner* — Robert M Kelly
(74) *Attorney, Agent, or Firm* — Wolf, Greenfield & Sacks, P.C.

(57) ABSTRACT

The present invention relates generally to genetically modified non-human animals and immunodeficient non-human animals characterized by restored complement-dependent cytotoxicity, as well as methods and compositions for assessment of therapeutic antibodies in the genetically modified immunodeficient non-human animals. In specific aspects, the present invention relates to immunodeficient non-obese diabetic (NOD), A/J, A/He, AKR, DBA/2, NZB/B1N, B10.D2/oSn and other mouse strains genetically modified to restore complement-dependent cytotoxicity which is lacking in the unmodified immunodeficient mice. In further specific aspects, the present invention relates to NOD.Cg-Prkdc$^{scid}$ IL2re$^{tm1Wjl}$/SzJ (NSG), NOD.Cg-Rag1$^{tm1Mom}$ Il2rg$^{tm1Wjl}$/SzJ (NRG) and NOD.Cg-Prkdc$^{scid}$ Il2rg$^{tm1Sug}$/JicTac (NOG) mice genetically modified to restore complement-dependent cytotoxicity which is lacking in unmodified NSG, NRG and NOG mice. Methods for assessment of therapeutic antibodies or putative therapeutic antibodies in the genetically modified immunodeficient mice characterized by an intact complement system are provided according to specific aspects of the present invention.

12 Claims, 8 Drawing Sheets
Specification includes a Sequence Listing.

(56) References Cited

OTHER PUBLICATIONS

Baxter et al., Complement lytic activity has no role in the pathogenesis of autoimmune diabetes in NOD mice. Diabetes. Nov. 1993;42(11):1574-8.

Bosma et al., The mouse mutation severe combined immune deficiency (scid) is on chromosome 16. Immunogenetics. 1989;29(1):54-7.

Christianson et al., Role of natural killer cells on engraftment of human lymphoid cells and on metastasis of human T-lymphoblastoid leukemia cells in C57BL/6J-scid mice and in C57BL/6J-scid bg mice. Cell Immunol. Aug. 1, 1996;171(2):186-99.

Ito et al., NOD/SCID/gamma(c)(null) mouse: an excellent recipient mouse model for engraftment of human cells. Blood. Nov. 1, 2002;100(9):3175-82.

Maykel et al., NOD-scidIl2rg (tm1Wjl) and NOD-Rag1 (null) Il2rg (tm1Wjl): a model for stromal cell-tumor cell interaction for human colon cancer. Dig Dis Sci. Jun. 2014;59(6):1169-79. doi: 10.1007/S10620-014-3168-5. Epub May 6, 2014.

Mombaerts et al., RAG-1-deficient mice have no mature B and T lymphocytes. Cell. Mar. 6, 1992;68(5):869-77.

Oettinger et al., RAG-1 and RAG-2, adjacent genes that synergistically activate V(D)J recombination. Science. Jun. 22, 1990;248(4962):1517-23.

Pearson et al., Non-obese diabetic-recombination activating gene-1 (NOD-Rag1 null) interleukin (IL)-2 receptor common gamma chain (IL2r gamma null) null mice: a radioresistant model for human lymphohaematopoietic engraftment. Clin Exp Immunol. Nov. 2008;154(2):270-84. doi: 10.1111/j.1365-2249.2008.03753.x. Epub Sep. 8, 2008.

Sato et al., A complement-dependent cytotoxicity-enhancing anti-CD20 antibody mediating potent antitumor activity in the humanized NOD/Shi-scid, IL-2Rγ(null) mouse lymphoma model. Cancer Immunol Immunother. Dec. 2010;59(12):1791-800. doi: 10.1007/s00262-010-0905-2. Epub Aug. 17, 2010.

Schatz et al., The V(D)J recombination activating gene, RAG-1. Cell. Dec. 22, 1989;59(6):1035-48.

Shultz et al., Human cancer growth and therapy in NOD/SCID/IL2Rgamma null (NSG) mice. Cold Spring Harb Protoc. Jul. 1, 2014;2014(7):694-708. doi: 10.1101/pdb.top073585. Author manuscript.

Shultz et al., Human lymphoid and myeloid cell development in NOD/LtSz-scid IL2R gamma null mice engrafted with mobilized human hemopoietic stem cells. J Immunol. May 15, 2005;174(10):6477-89.

Shultz et al., Multiple defects in innate and adaptive immunologic function in NOD/LtSz-scid mice. J Immunol. Jan. 1, 1995;154(1):180-91.

Takenaka et al., Polymorphism in Sirpa modulates engraftment of human hematopoietic stem cells. Nat Immunol. Dec. 2007;8(12):1313-23. Epub Nov. 4, 2007.

Verma et al., A novel hemolytic complement-sufficient NSG mouse model supports studies of complement-mediated antitumor activity in vivo. J Immunol Methods. Jul. 2017;446:47-53. doi: 10.1016/j.jim.2017.03.021. Epub Apr. 6, 2017. Author manuscript.

Yamauchi et al., Polymorphic Sirpa is the genetic determinant for NOD-based mouse lines to achieve efficient human cell engraftment. Blood. Feb. 21, 2013;121(8):1316-25. doi: 10.1182/blood-2012-06-440354. Epub Jan. 4, 2013.

GENETICALLY MODIFIED NON-HUMAN ANIMALS AND METHODS RELATING TO COMPLEMENT DEPENDENT CYTOTOXICITY

REFERENCE TO RELATED APPLICATIONS

This application is a continuation of U.S. patent application Ser. No. 15/736,951, now U.S. Pat. No. 10,701,911, filed Dec. 15, 2017, which is a national stage filing under 35 U.S.C. § 371 of international application number PCT/US2016/037882, filed Jun. 16, 2016, which claims priority to U.S. provisional application No. 62/180,369, filed Jun. 16, 2015, and U.S. provisional application No. 62/326,958, filed Apr. 25, 2016, the entire content of each of which is incorporated herein by reference.

FIELD OF THE INVENTION

The present invention relates generally to genetically modified non-human animals and immunodeficient non-human animals characterized by restored complement-dependent cytotoxicity, as well as methods and compositions for assessment of therapeutic antibodies in the genetically modified immunodeficient non-human animals. In specific aspects, the present invention relates to immunodeficient non-obese diabetic (NOD), A/J, A/He, AKR, DBA/2, NZB/B1N, B10.D2/oSn and other mouse strains genetically modified to restore complement-dependent cytotoxicity which is lacking in the unmodified immunodeficient mice. In further specific aspects, the present invention relates to NOD.Cg-Prkdc$^{scid}$ IL2rg$^{tm1Wjl}$/SzJ (NSG), NOD.Cg-Rag1$^{tm1Mom}$ Il2rg$^{tm1Wjl}$ SzJ (NRG) and NOD.Cg-Prkdc$^{scid}$ Il2rg$^{tm1Sug}$/JicTac (NOG) mice genetically modified to restore complement-dependent cytotoxicity which is lacking in unmodified NSG, NRG and NOG mice. Methods for assessment of therapeutic antibodies in the genetically modified immunodeficient mice characterized by an intact complement system, such as NSG, NRG and NOG mice characterized by an intact complement system are provided according to specific aspects of the present invention.

BACKGROUND OF THE INVENTION

Monoclonal antibodies (mAb) have emerged as a mainstream therapeutic option in the treatment of cancer. The Fc function of mAb is particularly important for mediating tumor cell killing through antibody-dependent cellular cytotoxicity (ADCC) 8220898.1 by natural killer (NK) cells and complement-dependent cytotoxicity (CDC). However, studies on mAb mediated CDC against tumor cells remain largely dependent on in vitro systems. NSG, NRG, NOG and other immunodeficient mice support enhanced engraftment of human tumors. However, lack of hemolytic complement due a 2-bp deletion in the coding region of the hemolytic complement (Hc) gene in several types of immunodeficient mice, such as NSG, NRG and NOG mice, prevents the evaluation of CDC activity in vivo in these mice.

There is a continuing need for methods and compositions for analysis of mAb-mediated CDC against tumor cells, to facilitate development of effective medical and pharmaceutical treatments of diseases such as cancer.

SUMMARY OF THE INVENTION

Genetically modified NOD mice are provided by the present invention wherein the genome of the mouse comprises a repaired C5 complement component structural gene such that the genetically modified NOD mouse expresses the C5 complement component structural gene and is characterized by an intact complement system.

Genetically modified immunodeficient mice are provided by the present invention wherein the genome of the genetically modified mice includes a repaired C5 complement component structural gene such that the genetically modified immunodeficient mice express the C5 complement component structural gene and are characterized by an intact complement system.

Genetically modified immunodeficient non-obese diabetic (NOD), A/J, A/He, AKR, DBA/2, NZB/B1N, or B10.D2/oSn mice are provided by the present invention wherein the genome of the genetically modified mice includes a repaired C5 complement component structural gene such that the genetically modified immunodeficient mice express the C5 complement component structural gene and are characterized by an intact complement system.

Genetically modified immunodeficient mice are provided by the present invention wherein the genome of the genetically modified mice includes a repaired C5 complement component structural gene such that the genetically modified immunodeficient mice express the C5 complement component structural gene and are characterized by an intact complement system, and wherein the mice have severe combined immunodeficiency.

Genetically modified immunodeficient mice are provided by the present invention wherein the genome of the genetically modified mice includes the scid mutation, and wherein the genome of the genetically modified mice includes a repaired C5 complement component structural gene such that the genetically modified immunodeficient mice express the C5 complement component structural gene and are characterized by an intact complement system.

Genetically modified immunodeficient mice are provided by the present invention wherein the genome of the genetically modified mice is homozygous for the scid mutation, and wherein the genome of the genetically modified mice includes a repaired C5 complement component structural gene such that the genetically modified immunodeficient mice express the C5 complement component structural gene and are characterized by an intact complement system.

Genetically modified immunodeficient mice are provided by the present invention wherein the genome of the genetically modified mice includes a repaired C5 complement component structural gene such that the genetically modified immunodeficient mice express the C5 complement component structural gene and are characterized by an intact complement system and an IL2 receptor gamma chain deficiency.

Genetically modified immunodeficient mice are provided by the present invention wherein the genome of the genetically modified mice includes an Il2rg mutation, and wherein the genome of the genetically modified mice include a repaired C5 complement component structural gene such that the genetically modified immunodeficient mice express the C5 complement component structural gene and are characterized by an intact complement system and an IL2 receptor gamma chain deficiency.

Genetically modified immunodeficient mice are provided by the present invention wherein the genome of the genetically modified mice is homozygous for an Il2rg mutation, and wherein the genome of the genetically modified mice includes a repaired C5 complement component structural gene such that the genetically modified immunodeficient mice express the C5 complement component structural gene and are characterized by an intact complement system and an IL2 receptor gamma chain deficiency.

Genetically modified immunodeficient mice are provided by the present invention wherein the genome of the genetically modified mice includes a repaired C5 complement component structural gene such that the genetically modified immunodeficient mice express the C5 complement component structural gene and are characterized by an intact complement system and a recombination activating gene 1 deficiency.

Genetically modified immunodeficient mice are provided by the present invention wherein the genome of the genetically modified mice includes the Rag1 mutation, and wherein the genome of the genetically modified mice includes a repaired C5 complement component structural gene such that the genetically modified immunodeficient mice express the C5 complement component structural gene and are characterized by an intact complement system and a RAG1 deficiency.

Genetically modified immunodeficient mice are provided by the present invention wherein the genome of the genetically modified mice is homozygous for the Rag1 mutation, and wherein the genome of the genetically modified mice includes a repaired C5 complement component structural gene such that the genetically modified immunodeficient mice express the C5 complement component structural gene and are characterized by an intact complement system and a RAG 1 deficiency.

Genetically modified immunodeficient mice are provided by the present invention wherein the genome of the genetically modified mice includes a repaired C5 complement component structural gene such that the genetically modified immunodeficient mice express the C5 complement component structural gene and are characterized by an intact complement system, and a recombination activating gene 2 (RAG 2) deficiency.

Genetically modified immunodeficient mice are provided by the present invention wherein the genome of the genetically modified mice includes a Rag2 mutation, and wherein the genome of the genetically modified mice includes a repaired C5 complement component structural gene such that the genetically modified immunodeficient mice express the C5 complement component structural gene and are characterized by an intact complement system and a RAG 2 deficiency.

Genetically modified immunodeficient mice are provided by the present invention wherein the genome of the genetically modified mice is homozygous for a Rag2 mutation, and wherein the genome of the genetically modified mice includes a repaired C5 complement component structural gene such that the genetically modified immunodeficient mice express the C5 complement component structural gene and are characterized by an intact complement system and a RAG 2 deficiency.

Genetically modified immunodeficient mice are provided by the present invention wherein the genome of the genetically modified mice includes a repaired C5 complement component structural gene such that the genetically modified immunodeficient mice express the C5 complement component structural gene and are characterized by an intact complement system, severe combined immunodeficiency and an IL2 receptor gamma chain deficiency.

Genetically modified immunodeficient mice are provided by the present invention wherein the genome of the genetically modified mice includes the scid mutation, wherein the animal has an IL2 receptor gamma chain deficiency, and wherein the genome of the genetically modified mice includes a repaired C5 complement component structural gene such that the genetically modified immunodeficient mice express the C5 complement component structural gene and are characterized by an intact complement system, severe combined immunodeficiency and an IL2 receptor gamma chain deficiency.

Genetically modified immunodeficient mice are provided by the present invention wherein the genome of the genetically modified mice is homozygous for the scid mutation, wherein the animal has an IL2 receptor gamma chain deficiency, and wherein the genome of the genetically modified mice includes a repaired C5 complement component structural gene such that the genetically modified immunodeficient mice express the C5 complement component structural gene and are characterized by an intact complement system, severe combined immunodeficiency and an IL2 receptor gamma chain deficiency.

Genetically modified immunodeficient mice are provided by the present invention wherein the genome of the genetically modified mice includes a repaired C5 complement component structural gene such that the genetically modified immunodeficient mice express the C5 complement component structural gene and are characterized by an intact complement system, and wherein the mice have a recombination activating gene 1 deficiency and an IL2 receptor gamma chain deficiency.

Genetically modified immunodeficient mice are provided by the present invention wherein the genome of the genetically modified mice includes a Rag1 mutation, wherein the animal has an IL2 receptor gamma chain deficiency, and wherein the genome of the genetically modified mice includes a repaired C5 complement component structural gene such that the genetically modified immunodeficient mice express the C5 complement component structural gene and are characterized by an intact complement system, a RAG 1 deficiency and an IL2 receptor gamma chain deficiency.

Genetically modified immunodeficient mice are provided by the present invention wherein the genome of the genetically modified mice is homozygous for a Rag1 mutation wherein the animal has an IL2 receptor gamma chain deficiency, and wherein the genome of the genetically modified mice includes a repaired C5 complement component structural gene such that the genetically modified immunodeficient mice express the C5 complement component structural gene and is characterized by an intact complement system, a RAG 1 deficiency and an IL2 receptor gamma chain deficiency.

Genetically modified immunodeficient mice are provided by the present invention wherein the genome of the genetically modified mice includes a repaired C5 complement component structural gene such that the genetically modified immunodeficient mice express the C5 complement component structural gene and are characterized by an intact complement system, and wherein the mice have a recombination activating gene 2 deficiency and an IL2 receptor gamma chain deficiency.

Genetically modified immunodeficient mice are provided by the present invention wherein the genome of the genetically modified mice includes a Rag2 mutation, wherein the animal has an IL2 receptor gamma chain deficiency, and wherein the genome of the genetically modified mice includes a repaired C5 complement component structural gene such that the genetically modified immunodeficient mice express the C5 complement component structural gene and are characterized by an intact complement system, a RAG 2 deficiency and an IL2 receptor gamma chain deficiency.

Genetically modified immunodeficient mice are provided by the present invention wherein the genome of the genetically modified mice is homozygous for a Rag2 mutation wherein the animal has an IL2 receptor gamma chain deficiency, and wherein the genome of the genetically modified mice includes a repaired C5 complement component structural gene such that the genetically modified immunodeficient mice express the C5 complement component structural gene and is characterized by an intact complement system, a RAG 2 deficiency and an IL2 receptor gamma chain deficiency.

Genetically modified immunodeficient non-human mice according to aspects of the present invention are immunodeficient NOD, A/J, A/He, AKR, DBA/2, NZB/B1N or B10.D2/oSn mice.

Genetically modified immunodeficient non-human mice according to aspects of the present invention are immunodeficient NOD mice.

Genetically modified immunodeficient NOD mice are provided by the present invention wherein the genetically modified immunodeficient NOD mice have a severe combined immunodeficiency, and wherein the genome of the genetically modified mice includes a repaired C5 complement component structural gene such that the genetically modified immunodeficient mice express the C5 complement component structural gene and are characterized by an intact complement system.

Genetically modified immunodeficient NOD mice are provided by the present invention wherein the genome of the genetically modified NOD mice includes the scid mutation, and wherein the genome of the genetically modified mice includes a repaired C5 complement component structural gene such that the genetically modified immunodeficient mice express the C5 complement component structural gene and are characterized by an intact complement system.

Genetically modified immunodeficient NOD mice are provided by the present invention wherein the genome of the genetically modified NOD mice is homozygous for the scid mutation, and wherein the genome of the genetically modified mice includes a repaired C5 complement component structural gene such that the genetically modified immunodeficient mice express the C5 complement component structural gene and are characterized by an intact complement system.

Genetically modified immunodeficient NOD mice are provided by the present invention wherein the animal has an IL2 receptor gamma chain deficiency, and wherein the genome of the genetically modified mice includes a repaired C5 complement component structural gene such that the genetically modified immunodeficient mice express the C5 complement component structural gene and are characterized by an intact complement system.

Genetically modified immunodeficient NOD mice are provided by the present invention wherein the genome of the genetically modified NOD mice includes an Il2rg mutation, and wherein the genome of the genetically modified mice includes a repaired C5 complement component structural gene such that the genetically modified immunodeficient mice express the C5 complement component structural gene and are characterized by an intact complement system and an IL2 receptor gamma chain deficiency.

Genetically modified immunodeficient NOD mice are provided by the present invention wherein the genome of the genetically modified NOD mice is homozygous for an Il2rg mutation, and wherein the genome of the genetically modified mice includes a repaired C5 complement component structural gene such that the genetically modified immunodeficient mice express the C5 complement component structural gene and are characterized by an intact complement system and an IL2 receptor gamma chain deficiency.

Genetically modified immunodeficient NOD mice are provided by the present invention wherein the animal has a RAG 1 deficiency, and wherein the genome of the genetically modified mice includes a repaired C5 complement component structural gene such that the genetically modified immunodeficient mice express the C5 complement component structural gene and are characterized by an intact complement system.

Genetically modified immunodeficient NOD mice are provided by the present invention wherein the genome of the genetically modified NOD mice includes a Rag1 mutation, and wherein the genome of the genetically modified mice includes a repaired C5 complement component structural gene such that the genetically modified immunodeficient mice express the C5 complement component structural gene and are characterized by an intact complement system and a RAG 1 deficiency.

Genetically modified immunodeficient NOD mice are provided by the present invention wherein the genome of the genetically modified NOD mice is homozygous for a Rag1 mutation, and wherein the genome of the genetically modified mice includes a repaired C5 complement component structural gene such that the genetically modified immunodeficient mice express the C5 complement component structural gene and are characterized by an intact complement system and a RAG 1 deficiency.

Genetically modified immunodeficient NOD mice are provided by the present invention wherein the animal has a RAG 2 deficiency, and wherein the genome of the genetically modified mice includes a repaired C5 complement component structural gene such that the genetically modified immunodeficient mice express the C5 complement component structural gene and are characterized by an intact complement system and a RAG 2 deficiency.

Genetically modified immunodeficient NOD mice are provided by the present invention wherein the genome of the genetically modified NOD mice includes a Rag2 mutation, and wherein the genome of the genetically modified mice includes a repaired C5 complement component structural gene such that the genetically modified immunodeficient mice express the C5 complement component structural gene and are characterized by an intact complement system and a RAG 2 deficiency.

Genetically modified immunodeficient NOD mice are provided by the present invention wherein the genome of the genetically modified NOD mice is homozygous for a Rag2 mutation, and wherein the genome of the genetically modified mice includes a repaired C5 complement component structural gene such that the genetically modified immunodeficient mice express the C5 complement component structural gene and is characterized by an intact complement system and a RAG 2 deficiency.

Genetically modified immunodeficient NOD mice are provided by the present invention wherein the genome of the genetically modified NOD mice is homozygous for the scid mutation, wherein the animal has an IL2 receptor gamma chain deficiency, and wherein the genome of the genetically modified mice includes a repaired C5 complement component structural gene such that the genetically modified immunodeficient mice express the C5 complement component structural gene and are characterized by an intact complement system, severe combined immunodeficiency and IL2 receptor gamma chain deficiency.

A NOD.Cg-Prkdc$^{scid}$Il2rg$^{tm1Wjl}$ Hc$^1$/SzJ (NSG-Hc$^1$) mouse is provided by the present invention including a repaired C5 complement component structural gene such that the mouse expresses the C5 complement component structural gene and is characterized by an intact complement system, a severe combined immunodeficiency and an IL2 receptor gamma chain deficiency.

Genetically modified immunodeficient NOD mice are provided by the present invention wherein the genome of the genetically modified NOD mice is homozygous for a Rag1 mutation, wherein the animal has an IL2 receptor gamma chain deficiency and wherein the genome of the genetically modified mice includes a repaired C5 complement component structural gene such that the genetically modified immunodeficient mice express the C5 complement component structural gene and are characterized by an intact complement system, a RAG 1 deficiency and an IL2 receptor gamma deficiency.

A NOD.Cg-Rag1$^{tm1Mom}$ Il2rg$^{tm1Wjl}$ Hc$^1$/SzJ (NRG-Hc$^1$) mouse is provided by the present invention which includes a repaired C5 complement component structural gene such that the mouse expresses the C5 complement component structural gene and is characterized by an intact complement system, a RAG1 deficiency and IL2 receptor gamma deficiency.

A NOD.Cg-Prkdc$^{scid}$ Il2rg$^{tm1Sug}$ Hc$^1$/JicTac (NOG-Hc$^1$) mouse is provided by the present invention which includes a repaired C5 complement component structural gene such that the mouse expresses the C5 complement component structural gene and is characterized by an intact complement system, a severe combined immunodeficiency and an IL2 receptor gamma chain deficiency.

Genetically modified immunodeficient NOD mice are provided by the present invention wherein the genome of the genetically modified NOD mice is homozygous for a Rag2 mutation, wherein the animal has an IL2 receptor gamma chain deficiency, and wherein the genome of the genetically modified mice includes a repaired C5 complement component structural gene such that the genetically modified immunodeficient mice express the C5 complement component structural gene and are characterized by an intact complement system, RAG 2 deficiency and IL2 receptor gamma chain deficiency.

Isolated cells of genetically modified immunodeficient mice are provided by the present invention, wherein the genome of the genetically modified mice includes a repaired C5 complement component structural gene such that the genetically modified immunodeficient non-human animals express the C5 complement component structural gene and is characterized by an intact complement system.

Isolated cells of a NSG-Hc$^1$ mouse including a repaired C5 complement component structural gene such that the mouse expresses the C5 complement component structural gene and is characterized by an intact complement system.

Isolated cells of a NRG-Hc$^1$ mouse including a repaired C5 complement component structural gene such that the mouse expresses the C5 complement component structural gene and is characterized by an intact complement system.

Isolated cells of a NOG-Hc$^1$ mouse including a repaired C5 complement component structural gene such that the mouse expresses the C5 complement component structural gene and is characterized by an intact complement system.

According to aspects of the present invention, genetically modified immunodeficient mice of the present invention further include xenograft tumor cells.

According to aspects of the present invention, genetically modified immunodeficient mice of the present invention further include human xenograft tumor cells.

According to aspects of the present invention, genetically modified immunodeficient mice of the present invention further include xenograft tumor cells of a cell line.

A NOD.Cg-Prkdc$^{scid}$Il2rg$^{tm1Wjl}$Hc$^1$/SzJ (NSG-Hc$^1$) mouse further including xenograft tumor cells is provided by the present invention.

A NOD.Cg-Prkdc$^{scid}$Il2rg$^{tm1Wjl}$Hc$^1$/SzJ (NSG-Hc$^1$) mouse further including human xenograft tumor cells is provided by the present invention.

A NOD.Cg-Prkdc$^{scid}$Il2rg$^{tm1Wjl}$Hc$^1$/SzJ (NSG-Hc$^1$) mouse further including xenograft tumor cells of a cell line is provided by the present invention.

A NOD.Cg-Rag1$^{tm1Mom}$Il2rg$^{tm1Wjl}$ Hc$^1$/SzJ (NRG-Hc$^1$) mouse further including xenograft tumor cells is provided by the present invention.

A NOD.Cg-Ragr$^{tm1Mom}$Il2rg$^{tm1Wjl}$ Hc$^1$/SzJ (NRG-Hc$^1$) mouse further including human xenograft tumor cells is provided by the present invention.

A NOD.Cg-Ragr$^{tm1Mom}$Il2rg$^{tm1Wjl}$ Hc$^1$/SzJ (NRG-Hc$^1$) mouse further including xenograft tumor cells of a cell line is provided by the present invention.

A NOD.Cg-Prkdc$^{scid}$ Il2rg$^{tm1Wjl}$ Hc$^1$/JicTac (NOG-Hc$^1$) mouse further including xenograft tumor cells is provided by the present invention.

A NOD.Cg-Prkdc$^{scid}$ Il2rg$^{tm1Wjl}$ Hc$^1$/JicTac (NOG-Hc$^1$) mouse further including human xenograft tumor cells is provided by the present invention.

Methods for producing a mouse model system for assessment of an anti-cancer therapeutic or putative anti-cancer therapeutic are provided according to aspects of the present invention which include providing a genetically modified immunodeficient mouse including a repaired C5 complement component structural gene such that the genetically modified immunodeficient mouse expresses the C5 complement component structural gene and is characterized by an intact complement system; and administering xenograft tumor cells to the genetically modified immunodeficient mouse.

Methods for producing a mouse model system for assessment of an anti-cancer therapeutic or putative anti-cancer therapeutic are provided according to aspects of the present invention which include providing a genetically modified immunodeficient non-obese diabetic (NOD), A/J, A/He, AKR, DBA/2, NZB/B1N, or B10.D2/oSn mouse including a repaired C5 complement component structural gene such that the genetically modified immunodeficient mouse expresses the C5 complement component structural gene and is characterized by an intact complement system; and administering xenograft tumor cells to the genetically modified immunodeficient mouse.

Methods for producing a mouse model system for assessment of an anti-cancer therapeutic or putative anti-cancer therapeutic are provided according to aspects of the present invention which include providing a genetically modified immunodeficient mouse including a repaired C5 complement component structural gene such that the genetically modified immunodeficient mouse expresses the C5 complement component structural gene and is characterized by an intact complement system, wherein the genetically modified immunodeficient mouse has severe combined immunodeficiency; and administering xenograft tumor cells to the genetically modified immunodeficient mouse.

Methods for producing a mouse model system for assessment of an anti-cancer therapeutic or putative anti-cancer therapeutic are provided according to aspects of the present invention which include providing a genetically modified immunodeficient mouse wherein the genome of the genetically modified immunodeficient mouse includes the scid mutation and wherein the genome of the genetically modified immunodeficient mouse includes a repaired C5 complement component structural gene such that the genetically modified immunodeficient mouse expresses the C5 complement component structural gene and is characterized by an intact complement system and has severe combined immunodeficiency; and administering xenograft tumor cells to the genetically modified immunodeficient mouse.

Methods for producing a mouse model system for assessment of an anti-cancer therapeutic or putative anti-cancer therapeutic are provided according to aspects of the present invention which include providing a genetically modified immunodeficient mouse wherein the genome of the genetically modified immunodeficient mouse is homozygous for the scid mutation and wherein the genome of the genetically modified mouse includes a repaired C5 complement component structural gene such that the genetically modified immunodeficient mouse expresses the C5 complement component structural gene and is characterized by an intact complement system and has severe combined immunodeficiency; and administering xenograft tumor cells to the genetically modified immunodeficient mouse.

Methods for producing a mouse model system for assessment of an anti-cancer therapeutic or putative anti-cancer therapeutic are provided according to aspects of the present invention which include providing a genetically modified immunodeficient mouse including a repaired C5 complement component structural gene such that the genetically modified immunodeficient mouse expresses the C5 complement component structural gene and is characterized by an intact complement system, wherein the genetically modified immunodeficient mouse has an IL2 receptor gamma chain deficiency; and administering xenograft tumor cells to the genetically modified immunodeficient mouse.

Methods for producing a mouse model system for assessment of an anti-cancer therapeutic or putative anti-cancer therapeutic are provided according to aspects of the present invention which include providing a genetically modified immunodeficient mouse wherein the genome of the genetically modified immunodeficient mouse includes an Il2rg mutation and wherein the genome of the genetically modified mouse includes a repaired C5 complement component structural gene such that the genetically modified immunodeficient mouse expresses the C5 complement component structural gene and is characterized by an intact complement system and has an IL2 receptor gamma chain deficiency; and administering xenograft tumor cells to the genetically modified immunodeficient mouse.

Methods for producing a mouse model system for assessment of an anti-cancer therapeutic or putative anti-cancer therapeutic are provided according to aspects of the present invention which include providing a genetically modified immunodeficient mouse wherein the genome of the genetically modified mouse is homozygous for an Il2rg mutation and wherein the genome of the genetically modified immunodeficient mouse includes a repaired C5 complement component structural gene such that the genetically modified immunodeficient mouse expresses the C5 complement component structural gene and is characterized by an intact complement system and has an IL2 receptor gamma chain deficiency; and administering xenograft tumor cells to the genetically modified immunodeficient mouse.

Methods for producing a mouse model system for assessment of an anti-cancer therapeutic or putative anti-cancer therapeutic are provided according to aspects of the present invention which include providing a genetically modified immunodeficient mouse including a repaired C5 complement component structural gene such that the genetically modified immunodeficient mouse expresses the C5 complement component structural gene and is characterized by an intact complement system, wherein the genetically modified immunodeficient mouse has a recombination activating gene 1 deficiency; and administering xenograft tumor cells to the genetically modified immunodeficient mouse.

Methods for producing a mouse model system for assessment of an anti-cancer therapeutic or putative anti-cancer therapeutic are provided according to aspects of the present invention which include providing a genetically modified immunodeficient mouse wherein the genome of the genetically modified immunodeficient mouse includes a Rag1 mutation and wherein the genome of the genetically modified immunodeficient mouse includes a repaired C5 complement component structural gene such that the genetically modified immunodeficient mouse expresses the C5 complement component structural gene and is characterized by an intact complement system and has a recombination activating gene 1 deficiency; and administering xenograft tumor cells to the genetically modified immunodeficient mouse.

Methods for producing a mouse model system for assessment of an anti-cancer therapeutic or putative anti-cancer therapeutic are provided according to aspects of the present invention which include providing a genetically modified immunodeficient mouse wherein the genome of the genetically modified immunodeficient mouse is homozygous for a Rag1 mutation and wherein the genome of the genetically modified immunodeficient mouse includes a repaired C5 complement component structural gene such that the genetically modified immunodeficient mouse expresses the C5 complement component structural gene and is characterized by an intact complement system and has a recombination activating gene 1 deficiency; and administering xenograft tumor cells to the genetically modified immunodeficient mouse.

Methods for producing a mouse model system for assessment of an anti-cancer therapeutic or putative anti-cancer therapeutic are provided according to aspects of the present invention which include providing a genetically modified immunodeficient mouse including a repaired C5 complement component structural gene such that the genetically modified immunodeficient mouse expresses the C5 complement component structural gene and is characterized by an intact complement system, wherein the genetically modified immunodeficient mouse has a recombination activating gene 2 deficiency; and administering xenograft tumor cells to the genetically modified immunodeficient mouse.

Methods for producing a mouse model system for assessment of an anti-cancer therapeutic or putative anti-cancer therapeutic are provided according to aspects of the present invention which include providing a genetically modified immunodeficient mouse wherein the genome of the genetically modified immunodeficient mouse includes a Rag2 mutation and wherein the genome of the genetically modified immunodeficient mouse includes a repaired C5 complement component structural gene such that the genetically modified immunodeficient mouse expresses the C5 complement component structural gene and is characterized by an intact complement system; and administering xenograft tumor cells to the genetically modified immunodeficient mouse.

Methods for producing a mouse model system for assessment of an anti-cancer therapeutic or putative anti-cancer therapeutic are provided according to aspects of the present invention which include providing a genetically modified immunodeficient mouse wherein the genome of the genetically modified immunodeficient mouse is homozygous for a Rag2 mutation and wherein the genome of the genetically modified mouse includes a repaired C5 complement component structural gene such that the genetically modified immunodeficient mouse expresses the C5 complement component structural gene and is characterized by an intact complement system and has a recombination activating gene 2 deficiency; and administering xenograft tumor cells to the genetically modified immunodeficient mouse.

Methods for producing a mouse model system for assessment of an anti-cancer therapeutic or putative anti-cancer therapeutic are provided according to aspects of the present invention which include providing a genetically modified immunodeficient mouse including a repaired C5 complement component structural gene such that the genetically modified immunodeficient mouse expresses the C5 complement component structural gene and is characterized by an intact complement system, wherein the genetically modified immunodeficient mouse has severe combined immunodeficiency and an IL2 receptor gamma chain deficiency; and administering xenograft tumor cells to the genetically modified immunodeficient mouse.

Methods for producing a mouse model system for assessment of an anti-cancer therapeutic or putative anti-cancer therapeutic are provided according to aspects of the present invention which include providing a genetically modified immunodeficient mouse wherein the genome of the genetically modified immunodeficient mouse includes the scid mutation and an Il2rg mutation, wherein the genome of the genetically modified immunodeficient mouse includes a repaired C5 complement component structural gene such that the genetically modified immunodeficient mouse expresses the C5 complement component structural gene and is characterized by an intact complement system, and wherein the genetically modified immunodeficient mouse has severe combined immunodeficiency and has an IL2 receptor gamma chain deficiency; and administering xenograft tumor cells to the genetically modified immunodeficient mouse.

Methods for producing a mouse model system for assessment of an anti-cancer therapeutic or putative anti-cancer therapeutic are provided according to aspects of the present invention which include providing a genetically modified immunodeficient mouse wherein the genome of the genetically modified immunodeficient mouse is homozygous for the scid mutation and an Il2rg mutation and wherein the genome of the genetically modified immunodeficient mouse includes a repaired C5 complement component structural gene such that the genetically modified immunodeficient mouse expresses the C5 complement component structural gene and is characterized by an intact complement system, and wherein the genetically modified immunodeficient mouse has severe combined immunodeficiency and has an IL2 receptor gamma chain deficiency; and administering xenograft tumor cells to the genetically modified immunodeficient mouse.

Methods for producing a mouse model system for assessment of an anti-cancer therapeutic or putative anti-cancer therapeutic are provided according to aspects of the present invention which include providing a genetically modified immunodeficient mouse including a repaired C5 complement component structural gene such that the genetically modified immunodeficient mouse expresses the C5 complement component structural gene and is characterized by an intact complement system, wherein the genetically modified immunodeficient mouse has a recombination activating gene 1 deficiency and an IL2 receptor gamma chain deficiency; and administering xenograft tumor cells to the genetically modified immunodeficient mouse.

Methods for producing a mouse model system for assessment of an anti-cancer therapeutic or putative anti-cancer therapeutic are provided according to aspects of the present invention which include providing a genetically modified immunodeficient mouse wherein the genome of the genetically modified immunodeficient mouse includes a Rag1 mutation and an Il2rg mutation, wherein the genome of the genetically modified immunodeficient mouse includes a repaired C5 complement component structural gene such that the genetically modified immunodeficient mouse expresses the C5 complement component structural gene and is characterized by an intact complement system, and wherein the genetically modified immunodeficient mouse has a recombination activating gene 1 deficiency and has an IL2 receptor gamma chain deficiency; and administering xenograft tumor cells to the genetically modified immunodeficient mouse.

Methods for producing a mouse model system for assessment of an anti-cancer therapeutic or putative anti-cancer therapeutic are provided according to aspects of the present invention which include providing a genetically modified immunodeficient mouse wherein the genome of the genetically modified immunodeficient mouse is homozygous for the Rag1 mutation and an Il2rg mutation and wherein the genome of the genetically modified immunodeficient mouse includes a repaired C5 complement component structural gene such that the genetically modified immunodeficient mouse expresses the C5 complement component structural gene and is characterized by an intact complement system, and wherein the genetically modified immunodeficient mouse has a recombination activating gene 1 deficiency and has an IL2 receptor gamma chain deficiency; and administering xenograft tumor cells to the genetically modified immunodeficient mouse.

Methods for producing a mouse model system for assessment of an anti-cancer therapeutic or putative anti-cancer therapeutic are provided according to aspects of the present invention which include providing a genetically modified immunodeficient mouse including a repaired C5 complement component structural gene such that the genetically modified immunodeficient mouse expresses the C5 complement component structural gene and is characterized by an intact complement system, wherein the genetically modified immunodeficient mouse has a recombination activating gene 2 deficiency and an IL2 receptor gamma chain deficiency; and administering xenograft tumor cells to the genetically modified immunodeficient mouse.

Methods for producing a mouse model system for assessment of an anti-cancer therapeutic or putative anti-cancer therapeutic are provided according to aspects of the present invention which include providing a genetically modified immunodeficient mouse wherein the genome of the genetically modified immunodeficient mouse includes a Rag2 mutation and an Il2rg mutation, wherein the genome of the genetically modified immunodeficient mouse includes a repaired C5 complement component structural gene such that the genetically modified immunodeficient mouse expresses the C5 complement component structural gene and is characterized by an intact complement system, and wherein the genetically modified immunodeficient mouse has a recombination activating gene 2 deficiency and has an IL2 receptor gamma chain deficiency; and administering xenograft tumor cells to the genetically modified immunodeficient mouse.

Methods for producing a mouse model system for assessment of an anti-cancer therapeutic or putative anti-cancer therapeutic are provided according to aspects of the present invention which include providing a genetically modified immunodeficient mouse wherein the genome of the genetically modified immunodeficient mouse is homozygous for the Rag2 mutation and an Il2rg mutation and wherein the genome of the genetically modified immunodeficient mouse includes a repaired C5 complement component structural gene such that the genetically modified immunodeficient mouse expresses the C5 complement component structural gene and is characterized by an intact complement system, and wherein the genetically modified immunodeficient mouse has a recombination activating gene 2 deficiency and has an IL2 receptor gamma chain deficiency; and administering xenograft tumor cells to the genetically modified immunodeficient mouse.

According to aspects of the present invention, the xenograft tumor cells administered in the methods for producing a mouse model system for assessment of an anti-cancer therapeutic or putative anti-cancer therapeutic are human xenograft tumor cells.

According to aspects of the present invention, the xenograft tumor cells administered in the methods for producing a mouse model system for assessment of an anti-cancer therapeutic or putative anti-cancer therapeutic are xenograft tumor cells of a cell line.

Methods for producing a mouse model system for assessment of an anti-cancer therapeutic or putative anti-cancer therapeutic are provided according to aspects of the present invention which include providing a genetically modified immunodeficient NOD mouse including a repaired C5 complement component structural gene such that the genetically modified immunodeficient NOD mouse expresses the C5 complement component structural gene and is characterized by an intact complement system, wherein the genetically modified immunodeficient NOD mouse has severe combined immunodeficiency; and administering xenograft tumor cells to the genetically modified immunodeficient NOD mouse.

Methods for producing a mouse model system for assessment of an anti-cancer therapeutic or putative anti-cancer therapeutic are provided according to aspects of the present invention which include providing a genetically modified immunodeficient NOD mouse wherein the genome of the genetically modified immunodeficient NOD mouse includes the scid mutation and wherein the genome of the genetically modified NOD mouse includes a repaired C5 complement component structural gene such that the genetically modified immunodeficient NOD mouse expresses the C5 complement component structural gene and is characterized by an intact complement system and severe combined immunodeficiency; and administering xenograft tumor cells to the genetically modified immunodeficient NOD mouse.

Methods for producing a mouse model system for assessment of an anti-cancer therapeutic or putative anti-cancer therapeutic are provided according to aspects of the present invention which include providing a genetically modified immunodeficient NOD mouse wherein the genome of the genetically modified immunodeficient NOD mouse is homozygous for the scid mutation and wherein the genome of the genetically modified immunodeficient NOD mouse includes a repaired C5 complement component structural gene such that the genetically modified immunodeficient mouse expresses the C5 complement component structural gene and is characterized by an intact complement system and severe combined immunodeficiency; and administering xenograft tumor cells to the genetically modified immunodeficient NOD mouse.

Methods for producing a mouse model system for assessment of an anti-cancer therapeutic or putative anti-cancer therapeutic are provided according to aspects of the present invention which include providing a genetically modified immunodeficient NOD mouse including a repaired C5 complement component structural gene such that the genetically modified immunodeficient NOD mouse expresses the C5 complement component structural gene and is characterized by an intact complement system, wherein the mouse has an IL2 receptor gamma chain deficiency; and administering xenograft tumor cells to the genetically modified immunodeficient NOD mouse.

Methods for producing a mouse model system for assessment of an anti-cancer therapeutic or putative anti-cancer therapeutic are provided according to aspects of the present invention which include providing a genetically modified immunodeficient NOD mouse wherein the genome of the genetically modified immunodeficient NOD mouse includes an Il2rg mutation and wherein the genome of the genetically modified NOD mouse includes a repaired C5 complement component structural gene such that the genetically modified immunodeficient NOD mouse expresses the C5 complement component structural gene and is characterized by an intact complement system and IL2 receptor gamma chain deficiency; and administering xenograft tumor cells to the genetically modified immunodeficient NOD mouse.

Methods for producing a mouse model system for assessment of an anti-cancer therapeutic or putative anti-cancer therapeutic are provided according to aspects of the present invention which include providing a genetically modified immunodeficient NOD mouse wherein the genome of the genetically modified NOD mouse is homozygous for an Il2rg mutation and wherein the genome of the genetically modified NOD mouse includes a repaired C5 complement component structural gene such that the genetically modified immunodeficient NOD mouse expresses the C5 complement component structural gene and is characterized by an intact complement system and IL2 receptor gamma chain deficiency; and administering xenograft tumor cells to the genetically modified immunodeficient NOD mouse.

Methods for producing a mouse model system for assessment of an anti-cancer therapeutic or putative anti-cancer therapeutic are provided according to aspects of the present invention which include providing a genetically modified immunodeficient NOD mouse including a repaired C5 complement component structural gene such that the genetically modified immunodeficient NOD mouse expresses the C5 complement component structural gene and is characterized by an intact complement system, wherein the genetically modified immunodeficient NOD mouse has a recombination activating gene 1 deficiency; and administering xenograft tumor cells to the genetically modified immunodeficient NOD mouse.

Methods for producing a mouse model system for assessment of an anti-cancer therapeutic or putative anti-cancer therapeutic are provided according to aspects of the present invention which include providing a genetically modified immunodeficient NOD mouse wherein the genome of the genetically modified NOD mouse includes a Rag1 mutation and wherein the genome of the genetically modified NOD mouse includes a repaired C5 complement component structural gene such that the genetically modified immunodeficient NOD mouse expresses the C5 complement component structural gene and is characterized by an intact complement system and recombination activating gene 1 deficiency; and administering xenograft tumor cells to the genetically modified immunodeficient NOD mouse.

Methods for producing a mouse model system for assessment of an anti-cancer therapeutic or putative anti-cancer therapeutic are provided according to aspects of the present invention which include providing a genetically modified immunodeficient NOD mouse wherein the genome of the genetically modified immunodeficient NOD mouse is homozygous for a Rag1 mutation and wherein the genome of the genetically modified NOD mouse includes a repaired C5 complement component structural gene such that the genetically modified immunodeficient NOD mouse expresses the C5 complement component structural gene and is characterized by an intact complement system and recombination activating gene 1 deficiency; and administering xenograft tumor cells to the genetically modified NOD immunodeficient mouse.

Methods for producing a mouse model system for assessment of an anti-cancer therapeutic or putative anti-cancer therapeutic are provided according to aspects of the present invention which include providing a genetically modified immunodeficient NOD mouse including a repaired C5 complement component structural gene such that the genetically modified immunodeficient NOD mouse expresses the C5 complement component structural gene and is characterized by an intact complement system, wherein the genetically modified immunodeficient NOD mouse has a recombination activating gene 2 deficiency; and administering xenograft tumor cells to the genetically modified immunodeficient NOD mouse.

Methods for producing a mouse model system for assessment of an anti-cancer therapeutic or putative anti-cancer therapeutic are provided according to aspects of the present invention which include providing a genetically modified immunodeficient NOD mouse wherein the genome of the genetically modified immunodeficient NOD mouse includes a Rag2 mutation and wherein the genome of the genetically modified NOD mouse includes a repaired C5 complement component structural gene such that the genetically modified immunodeficient NOD mouse expresses the C5 complement component structural gene and is characterized by an intact complement system and recombination activating gene 2 deficiency; and administering xenograft tumor cells to the genetically modified immunodeficient NOD mouse.

Methods for producing a mouse model system for assessment of an anti-cancer therapeutic or putative anti-cancer therapeutic are provided according to aspects of the present invention which include providing a genetically modified immunodeficient NOD mouse wherein the genome of the genetically modified immunodeficient NOD mouse is homozygous for a Rag2 mutation and wherein the genome of the genetically modified immunodeficient NOD mouse includes a repaired C5 complement component structural gene such that the genetically modified immunodeficient NOD mouse expresses the C5 complement component structural gene and is characterized by an intact complement system and recombination activating gene 2 deficiency; and administering xenograft tumor cells to the genetically modified immunodeficient NOD mouse.

Methods for producing a mouse model system for assessment of an anti-cancer therapeutic or putative anti-cancer therapeutic are provided according to aspects of the present invention which include providing a genetically modified immunodeficient NOD mouse including a repaired C5 complement component structural gene such that the genetically modified immunodeficient NOD mouse expresses the C5 complement component structural gene and is characterized by an intact complement system, wherein the genetically modified immunodeficient NOD mouse has severe combined immunodeficiency and an IL2 receptor gamma chain deficiency; and administering xenograft tumor cells to the genetically modified immunodeficient NOD mouse.

Methods for producing a mouse model system for assessment of an anti-cancer therapeutic or putative anti-cancer therapeutic are provided according to aspects of the present invention which include providing a genetically modified immunodeficient NOD mouse wherein the genome of the genetically modified immunodeficient NOD mouse includes the scid mutation and an Il2rg mutation, wherein the genome of the genetically modified mice includes a repaired C5 complement component structural gene such that the genetically modified immunodeficient NOD mouse expresses the C5 complement component structural gene and is characterized by an intact complement system, and wherein the genetically modified immunodeficient NOD mouse has severe combined immunodeficiency and has an IL2 receptor gamma chain deficiency; and administering xenograft tumor cells to the genetically modified immunodeficient NOD mouse.

Methods for producing a mouse model system for assessment of an anti-cancer therapeutic or putative anti-cancer therapeutic are provided according to aspects of the present invention which include providing a genetically modified immunodeficient NOD mouse wherein the genome of the genetically modified immunodeficient NOD mouse is homozygous for the scid mutation and an Il2rg mutation and wherein the genome of the genetically modified immunodeficient NOD mouse includes a repaired C5 complement component structural gene such that the genetically modified immunodeficient NOD mouse expresses the C5 complement component structural gene and is characterized by an intact complement system, and wherein the genetically modified immunodeficient NOD mouse has severe combined immunodeficiency and has an IL2 receptor gamma chain deficiency; and administering xenograft tumor cells to the genetically modified immunodeficient NOD mouse.

Methods for producing a mouse model system for assessment of an anti-cancer therapeutic or putative anti-cancer therapeutic are provided according to aspects of the present invention which include providing a genetically modified immunodeficient NOD mouse including a repaired C5 complement component structural gene such that the genetically modified immunodeficient NOD mouse expresses the C5 complement component structural gene and is characterized by an intact complement system, wherein the genetically modified immunodeficient NOD mouse has a recombination activating gene 1 deficiency and an IL2 receptor gamma chain deficiency; and administering xenograft tumor cells to the genetically modified immunodeficient NOD mouse.

Methods for producing a mouse model system for assessment of an anti-cancer therapeutic or putative anti-cancer therapeutic are provided according to aspects of the present invention which include providing a genetically modified immunodeficient NOD mouse wherein the genome of the genetically immunodeficient modified NOD mouse includes a Rag1 mutation, wherein the genome of the genetically modified immunodeficient NOD mouse includes a repaired C5 complement component structural gene such that the genetically modified immunodeficient NOD mouse expresses the C5 complement component structural gene and is characterized by an intact complement system, and wherein the genetically modified immunodeficient NOD mouse has an IL2 receptor gamma chain deficiency and a recombination activating gene 1 deficiency; and administering xenograft tumor cells to the genetically modified immunodeficient NOD mouse.

Methods for producing a mouse model system for assessment of an anti-cancer therapeutic or putative anti-cancer therapeutic are provided according to aspects of the present invention which include providing a genetically modified immunodeficient NOD mouse wherein the genome of the genetically modified immunodeficient NOD mouse is homozygous for a Rag1 mutation and wherein the genome of the genetically modified immunodeficient NOD mouse includes a repaired C5 complement component structural gene such that the genetically modified immunodeficient NOD mouse expresses the C5 complement component structural gene and is characterized by an intact complement system, and wherein the mouse has an IL2 receptor gamma chain deficiency and a recombination activating gene 1 deficiency; and administering xenograft tumor cells to the genetically modified immunodeficient NOD mouse.

Methods for producing a mouse model system for assessment of an anti-cancer therapeutic or putative anti-cancer therapeutic are provided according to aspects of the present invention which include providing a genetically modified immunodeficient NOD mouse including a repaired C5 complement component structural gene such that the genetically modified immunodeficient NOD mouse expresses the C5 complement component structural gene and is characterized by an intact complement system, wherein the genetically modified immunodeficient NOD mouse has a recombination activating gene 2 deficiency and an IL2 receptor gamma chain deficiency; and administering xenograft tumor cells to the genetically modified immunodeficient NOD mouse.

Methods for producing a mouse model system for assessment of an anti-cancer therapeutic or putative anti-cancer therapeutic are provided according to aspects of the present invention which include providing a genetically modified immunodeficient NOD mouse wherein the genome of the genetically immunodeficient modified NOD mouse includes a Rag2 mutation, wherein the genome of the genetically modified immunodeficient NOD mouse includes a repaired C5 complement component structural gene such that the genetically modified immunodeficient NOD mouse expresses the C5 complement component structural gene and is characterized by an intact complement system, and wherein the genetically modified immunodeficient NOD mouse has an IL2 receptor gamma chain deficiency and a recombination activating gene 2 deficiency; and administering xenograft tumor cells to the genetically modified immunodeficient NOD mouse.

Methods for producing a mouse model system for assessment of an anti-cancer therapeutic or putative anti-cancer therapeutic are provided according to aspects of the present invention which include providing a genetically modified immunodeficient NOD mouse wherein the genome of the genetically modified immunodeficient NOD mouse is homozygous for a Rag2 mutation and wherein the genome of the genetically modified immunodeficient NOD mouse includes a repaired C5 complement component structural gene such that the genetically modified immunodeficient NOD mouse expresses the C5 complement component structural gene and is characterized by an intact complement system, and wherein the mouse has an IL2 receptor gamma chain deficiency and a recombination activating gene 2 deficiency; and administering xenograft tumor cells to the genetically modified immunodeficient NOD mouse.

Methods for producing a mouse model system for assessment of an anti-cancer therapeutic or putative anti-cancer therapeutic are provided according to aspects of the present invention which include providing a NSG-Hc$^1$ mouse wherein the genome of the NSG-Hc$^1$ mouse includes a repaired C5 complement component structural gene such that the NSG-Hc$^1$ mouse expresses the C5 complement component structural gene and is characterized by an intact complement system; and administering xenograft tumor cells to the NSG-Hc$^1$ mouse wherein the genome of the NSG-Hc$^1$ mouse includes a repaired C5 complement component structural gene such that the NSG-Hc$^1$ mouse expresses the C5 complement component structural gene and is characterized by an intact complement system.

Methods for producing a mouse model system for assessment of an anti-cancer therapeutic or putative anti-cancer therapeutic are provided according to aspects of the present invention which include providing a NRG-Hc$^1$ mouse wherein the genome of the NRG-Hc$^1$ mouse includes a repaired C5 complement component structural gene such that the NRG-Hc$^1$ mouse expresses the C5 complement component structural gene and is characterized by an intact complement system; and administering xenograft tumor cells to the NRG-Hc$^1$ mouse wherein the genome of the NRG-Hc$^1$ mouse includes a repaired C5 complement component structural gene such that the NRG-Hc$^1$ mouse expresses the C5 complement component structural gene and is characterized by an intact complement system.

Methods for producing a mouse model system for assessment of an anti-cancer therapeutic or putative anti-cancer therapeutic are provided according to aspects of the present invention which include providing a NOG-Hc$^1$ mouse wherein the genome of the NOG-Hc$^1$ mouse includes a repaired C5 complement component structural gene such that the NOG-Hc$^1$ mouse expresses the C5 complement component structural gene and is characterized by an intact complement system; and administering xenograft tumor cells to the NOG-Hc$^1$ mouse wherein the genome of the NOG-Hc$^1$ mouse includes a repaired C5 complement component structural gene such that the NOG-Hc$^1$ mouse expresses the C5 complement component structural gene and is characterized by an intact complement system.

Methods for assessing the effect of an anti-cancer therapeutic or putative anti-cancer therapeutic according to aspects of the present invention include providing a genetically modified immunodeficient mouse comprising a repaired C5 complement component structural gene such that the genetically modified immunodeficient mouse expresses the C5 complement component structural gene and is characterized by an intact complement system; administering xenograft tumor cells to the genetically modified immunodeficient mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for assessing the effect of an anti-cancer therapeutic or putative anti-cancer therapeutic according to aspects of the present invention include providing a genetically modified immunodeficient non-obese diabetic (NOD), A/J, A/He, AKR, DBA/2, NZB/B1N or B10.D2/oSn mouse comprising a repaired C5 complement component structural gene such that the genetically modified immunodeficient mouse expresses the C5 complement component structural gene and is characterized by an intact complement system; administering xenograft tumor cells to the genetically modified immunodeficient mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient mouse including a repaired C5 complement component structural gene such that the genetically modified immunodeficient mouse expresses the C5 complement component structural gene and is characterized by an intact complement system; administering xenograft tumor cells to the genetically modified immunodeficient mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient mouse including a repaired C5 complement component structural gene such that the genetically modified immunodeficient mouse expresses the C5 complement component structural gene and is characterized by an intact complement system, wherein the genetically modified immunodeficient mouse has severe combined immunodeficiency; administering xenograft tumor cells to the genetically modified immunodeficient mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient mouse wherein the genome of the genetically modified immunodeficient mouse includes the scid mutation and wherein the genome of the genetically modified immunodeficient mouse includes a repaired C5 complement component structural gene such that the genetically modified immunodeficient mouse expresses the C5 complement component structural gene and is characterized by an intact complement system and has severe combined immunodeficiency; administering xenograft tumor cells to the genetically modified immunodeficient mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient mouse wherein the genome of the genetically modified immunodeficient mouse is homozygous for the scid mutation and wherein the genome of the genetically modified mouse includes a repaired C5 complement component structural gene such that the genetically modified immunodeficient mouse expresses the C5 complement component structural gene and is characterized by an intact complement system and has severe combined immunodeficiency; administering xenograft tumor cells to the genetically modified immunodeficient mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient mouse including a repaired C5 complement component structural gene such that the genetically modified immunodeficient mouse expresses the C5 complement component structural gene and is characterized by an intact complement system, wherein the genetically modified immunodeficient mouse has an IL2 receptor gamma chain deficiency; administering xenograft tumor cells to the genetically modified immunodeficient mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient mouse wherein the genome of the genetically modified immunodeficient mouse includes an Il2rg mutation and wherein the genome of the genetically modified mouse includes a repaired C5 complement component structural gene such that the genetically modified immunodeficient mouse expresses the C5 complement component structural gene and is characterized by an intact complement system and has an IL2 receptor gamma chain deficiency; administering xenograft tumor cells to the genetically modified immunodeficient mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient mouse wherein the genome of the genetically modified mouse is homozygous for an Il2rg mutation and wherein the genome of the genetically modified immunodeficient mouse includes a repaired C5 complement component structural gene such that the genetically modified immunodeficient mouse expresses the C5 complement component structural gene and is characterized by an intact complement system and has an IL2 receptor gamma chain deficiency; administering xenograft tumor cells to the genetically modified immunodeficient mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient mouse including a repaired C5 complement component structural gene such that the genetically modified immunodeficient mouse expresses the C5 complement component structural gene and is characterized by an intact complement system, wherein the genetically modified immunodeficient mouse has a recombination activating gene 1 deficiency; administering xenograft tumor cells to the genetically modified immunodeficient mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient mouse wherein the genome of the genetically modified immunodeficient mouse includes a Rag1 mutation and wherein the genome of the genetically modified immunodeficient mouse includes a repaired C5 complement component structural gene such that the genetically modified immunodeficient mouse expresses the C5 complement component structural gene and is characterized by an intact complement system and has a recombination activating gene 1 deficiency; administering xenograft tumor cells to the genetically modified immunodeficient mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient mouse wherein the genome of the genetically modified immunodeficient mouse is homozygous for a Rag1 mutation and wherein the genome of the genetically modified immunodeficient mouse includes a repaired C5 complement component structural gene such that the genetically modified immunodeficient mouse expresses the C5 complement component structural gene and is characterized by an intact complement system and has a recombination activating gene 1 deficiency; administering xenograft tumor cells to the genetically modified immunodeficient mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient mouse including a repaired C5 complement component structural gene such that the genetically modified immunodeficient mouse expresses the C5 complement component structural gene and is characterized by an intact complement system, wherein the genetically modified immunodeficient mouse has a recombination activating gene 2 deficiency; administering xenograft tumor cells to the genetically modified immunodeficient mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient mouse wherein the genome of the genetically modified immunodeficient mouse includes a Rag2 mutation and wherein the genome of the genetically modified immunodeficient mouse includes a repaired C5 complement component structural gene such that the genetically modified immunodeficient mouse expresses the C5 complement component structural gene and is characterized by an intact complement system; administering xenograft tumor cells to the genetically modified immunodeficient mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient mouse wherein the genome of the genetically modified immunodeficient mouse is homozygous for a Rag2 mutation and wherein the genome of the genetically modified mouse includes a repaired C5 complement component structural gene such that the genetically modified immunodeficient mouse expresses the C5 complement component structural gene and is characterized by an intact complement system and has a recombination activating gene 2 deficiency; administering xenograft tumor cells to the genetically modified immunodeficient mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient mouse including a repaired C5 complement component structural gene such that the genetically modified immunodeficient mouse expresses the C5 complement component structural gene and is characterized by an intact complement system, wherein the genetically modified immunodeficient mouse has severe combined immunodeficiency and an IL2 receptor gamma chain deficiency; administering xenograft tumor cells to the genetically modified immunodeficient mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient mouse wherein the genome of the genetically modified immunodeficient mouse includes the scid mutation and an Il2rg mutation, wherein the genome of the genetically modified immunodeficient mouse includes a repaired C5 complement component structural gene such that the genetically modified immunodeficient mouse expresses the C5 complement component structural gene and is characterized by an intact complement system, and wherein the genetically modified immunodeficient mouse has severe combined immunodeficiency and has an IL2 receptor gamma chain deficiency; administering xenograft tumor cells to the genetically modified immunodeficient mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient mouse wherein the genome of the genetically modified immunodeficient mouse is homozygous for the scid mutation and an Il2rg mutation and wherein the genome of the genetically modified immunodeficient mouse includes a repaired C5 complement component structural gene such that the genetically modified immunodeficient mouse expresses the C5 complement component structural gene and is characterized by an intact complement system, and wherein the genetically modified immunodeficient mouse has severe combined immunodeficiency and has an IL2 receptor gamma chain deficiency; administering xenograft tumor cells to the genetically modified immunodeficient mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient mouse including a repaired C5 complement component structural gene such that the genetically modified immunodeficient mouse expresses the C5 complement component structural gene and is characterized by an intact complement system, wherein the genetically modified immunodeficient mouse has a recombination activating gene 1 deficiency and an IL2 receptor gamma chain deficiency; administering xenograft tumor cells to the genetically modified immunodeficient mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient mouse wherein the genome of the genetically modified immunodeficient mouse includes a Rag1 mutation and an Il2rg mutation, wherein the genome of the genetically modified immunodeficient mouse includes a repaired C5 complement component structural gene such that the genetically modified immunodeficient mouse expresses the C5 complement component structural gene and is characterized by an intact complement system, and wherein the genetically modified immunodeficient mouse has a recombination activating gene 1 deficiency and has an IL2 receptor gamma chain deficiency; administering xenograft tumor cells to the genetically modified immunodeficient mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient mouse wherein the genome of the genetically modified immunodeficient mouse is homozygous for the Rag1 mutation and an Il2rg mutation and wherein the genome of the genetically modified immunodeficient mouse includes a repaired C5 complement component structural gene such that the genetically modified immunodeficient mouse expresses the C5 complement component structural gene and is characterized by an intact complement system, and wherein the genetically modified immunodeficient mouse has a recombination activating gene 1 deficiency and has an IL2 receptor gamma chain deficiency; administering xenograft tumor cells to the genetically modified immunodeficient mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient mouse including a repaired C5 complement component structural gene such that the genetically modified immunodeficient mouse expresses the C5 complement component structural gene and is characterized by an intact complement system, wherein the genetically modified immunodeficient mouse has a recombination activating gene 2 deficiency and an IL2 receptor gamma chain deficiency; administering xenograft tumor cells to the genetically modified immunodeficient mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient mouse wherein the genome of the genetically modified immunodeficient mouse includes a Rag2 mutation and an Il2rg mutation, wherein the genome of the genetically modified immunodeficient mouse includes a repaired C5 complement component structural gene such that the genetically modified immunodeficient mouse expresses the C5 complement component structural gene and is characterized by an intact complement system, and wherein the genetically modified immunodeficient mouse has a recombination activating gene 2 deficiency and has an IL2 receptor gamma chain deficiency; administering xenograft tumor cells to the genetically modified immunodeficient mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient mouse wherein the genome of the genetically modified immunodeficient mouse is homozygous for the Rag2 mutation and an Il2rg mutation and wherein the genome of the genetically modified immunodeficient mouse includes a repaired C5 complement component structural gene such that the genetically modified immunodeficient mouse expresses the C5 complement component structural gene and is characterized by an intact complement system, and wherein the genetically modified immunodeficient mouse has a recombination activating gene 2 deficiency and has an IL2 receptor gamma chain deficiency; administering xenograft tumor cells to the genetically modified immunodeficient mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient NOD mouse including a repaired C5 complement component structural gene such that the genetically modified immunodeficient NOD mouse expresses the C5 complement component structural gene and is characterized by an intact complement system, wherein the genetically modified immunodeficient NOD mouse has severe combined immunodeficiency; administering xenograft tumor cells to the genetically modified immunodeficient NOD mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient NOD mouse wherein the genome of the genetically modified immunodeficient NOD mouse includes the scid mutation and wherein the genome of the genetically modified NOD mouse includes a repaired C5 complement component structural gene such that the genetically modified immunodeficient NOD mouse expresses the C5 complement component structural gene and is characterized by an intact complement system and severe combined immunodeficiency; administering xenograft tumor cells to the genetically modified immunodeficient NOD mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient NOD mouse wherein the genome of the genetically modified immunodeficient NOD mouse is homozygous for the scid mutation and wherein the genome of the genetically modified immunodeficient NOD mouse includes a repaired C5 complement component structural gene such that the genetically modified immunodeficient mouse expresses the C5 complement component structural gene and is characterized by an intact complement system and severe combined immunodeficiency; administering xenograft tumor cells to the genetically modified immunodeficient NOD mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient NOD mouse including a repaired C5 complement component structural gene such that the genetically modified immunodeficient NOD mouse expresses the C5 complement component structural gene and is characterized by an intact complement system, wherein the mouse has an IL2 receptor gamma chain deficiency; administering xenograft tumor cells to the genetically modified immunodeficient NOD mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient NOD mouse wherein the genome of the genetically modified immunodeficient NOD mouse includes an Il2rg mutation and wherein the genome of the genetically modified NOD mouse includes a repaired C5 complement component structural gene such that the genetically modified immunodeficient NOD mouse expresses the C5 complement component structural gene and is characterized by an intact complement system and IL2 receptor gamma chain deficiency; administering xenograft tumor cells to the genetically modified immunodeficient NOD mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient NOD mouse wherein the genome of the genetically modified NOD mouse is homozygous for an Il2rg mutation and wherein the genome of the genetically modified NOD mouse includes a repaired C5 complement component structural gene such that the genetically modified immunodeficient NOD mouse expresses the C5 complement component structural gene and is characterized by an intact complement system and IL2 receptor gamma chain deficiency; administering xenograft tumor cells to the genetically modified immunodeficient NOD mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient NOD mouse including a repaired C5 complement component structural gene such that the genetically modified immunodeficient NOD mouse expresses the C5 complement component structural gene and is characterized by an intact complement system, wherein the genetically modified immunodeficient NOD mouse has a recombination activating gene 1 deficiency; administering xenograft tumor cells to the genetically modified immunodeficient NOD mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient NOD mouse wherein the genome of the genetically modified NOD mouse includes a Rag1 mutation and wherein the genome of the genetically modified NOD mouse includes a repaired C5 complement component structural gene such that the genetically modified immunodeficient NOD mouse expresses the C5 complement component structural gene and is characterized by an intact complement system and recombination activating gene 1 deficiency; administering xenograft tumor cells to the genetically modified immunodeficient NOD mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient NOD mouse wherein the genome of the genetically modified immunodeficient NOD mouse is homozygous for a Rag1 mutation and wherein the genome of the genetically modified NOD mouse includes a repaired C5 complement component structural gene such that the genetically modified immunodeficient NOD mouse expresses the C5 complement component structural gene and is characterized by an intact complement system and recombination activating gene 1 deficiency; administering xenograft tumor cells to the genetically modified immunodeficient NOD mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient NOD mouse including a repaired C5 complement component structural gene such that the genetically modified immunodeficient NOD mouse expresses the C5 complement component structural gene and is characterized by an intact complement system, wherein the genetically modified immunodeficient NOD mouse has a recombination activating gene 2 deficiency; administering xenograft tumor cells to the genetically modified immunodeficient NOD mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient NOD mouse wherein the genome of the genetically modified immunodeficient NOD mouse includes a Rag2 mutation and wherein the genome of the genetically modified NOD mouse includes a repaired C5 complement component structural gene such that the genetically modified immunodeficient NOD mouse expresses the C5 complement component structural gene and is characterized by an intact complement system and recombination activating gene 2 deficiency; administering xenograft tumor cells to the genetically modified immunodeficient NOD mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient NOD mouse wherein the genome of the genetically modified NOD mouse is homozygous for a Rag2 mutation and wherein the genome of the genetically modified immunodeficient NOD mouse includes a repaired C5 complement component structural gene such that the genetically modified immunodeficient NOD mouse expresses the C5 complement component structural gene and is characterized by an intact complement system and recombination activating gene 2 deficiency; administering xenograft tumor cells to the genetically modified immunodeficient NOD mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient NOD mouse including a repaired C5 complement component structural gene such that the genetically modified immunodeficient NOD mouse expresses the C5 complement component structural gene and is characterized by an intact complement system, wherein the genetically modified immunodeficient NOD mouse has severe combined immunodeficiency and an IL2 receptor gamma chain deficiency; administering xenograft tumor cells to the genetically modified immunodeficient NOD mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient NOD mouse wherein the genome of the genetically modified immunodeficient NOD mouse includes the scid mutation and an Il2rg mutation, wherein the genome of the genetically modified mice includes a repaired C5 complement component structural gene such that the genetically modified immunodeficient NOD mouse expresses the C5 complement component structural gene and is characterized by an intact complement system, and wherein the genetically modified immunodeficient NOD mouse has severe combined immunodeficiency and has an IL2 receptor gamma chain deficiency; administering xenograft tumor cells to the genetically modified immunodeficient NOD mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient NOD mouse wherein the genome of the genetically modified immunodeficient NOD mouse is homozygous for the scid mutation and an Il2rg mutation and wherein the genome of the genetically modified immunodeficient NOD mouse includes a repaired C5 complement component structural gene such that the genetically modified immunodeficient NOD mouse expresses the C5 complement component structural gene and is characterized by an intact complement system, and wherein the genetically modified immunodeficient NOD mouse has severe combined immunodeficiency and has an IL2 receptor gamma chain deficiency; administering xenograft tumor cells to the genetically modified immunodeficient NOD mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient NOD mouse including a repaired C5 complement component structural gene such that the genetically modified immunodeficient NOD mouse expresses the C5 complement component structural gene and is characterized by an intact complement system, wherein the genetically modified immunodeficient NOD mouse has a recombination activating gene 1 deficiency and an IL2 receptor gamma chain deficiency; administering xenograft tumor cells to the genetically modified immunodeficient NOD mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient NOD mouse wherein the genome of the genetically immunodeficient modified NOD mouse includes a Rag1 mutation, wherein the genome of the genetically modified immunodeficient NOD mouse includes a repaired C5 complement component structural gene such that the genetically modified immunodeficient NOD mouse expresses the C5 complement component structural gene and is characterized by an intact complement system, and wherein the genetically modified immunodeficient NOD mouse has an IL2 receptor gamma chain deficiency and a recombination activating gene 1 deficiency; administering xenograft tumor cells to the genetically modified immunodeficient NOD mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient NOD mouse wherein the genome of the genetically modified immunodeficient NOD mouse is homozygous for a Rag1 mutation and wherein the genome of the genetically modified immunodeficient NOD mouse includes a repaired C5 complement component structural gene such that the genetically modified immunodeficient NOD mouse expresses the C5 complement component structural gene and is characterized by an intact complement system, and wherein the mouse has an IL2 receptor gamma chain deficiency and a recombination activating gene 1 deficiency; administering xenograft tumor cells to the genetically modified immunodeficient NOD mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient NOD mouse including a repaired C5 complement component structural gene such that the genetically modified immunodeficient NOD mouse expresses the C5 complement component structural gene and is characterized by an intact complement system, wherein the genetically modified immunodeficient NOD mouse has a recombination activating gene 2 deficiency and an IL2 receptor gamma chain deficiency; administering xenograft tumor cells to the genetically modified immunodeficient NOD mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient NOD mouse wherein the genome of the genetically immunodeficient modified NOD mouse includes a Rag2 mutation, wherein the genome of the genetically modified immunodeficient NOD mouse includes a repaired C5 complement component structural gene such that the genetically modified immunodeficient NOD mouse expresses the C5 complement component structural gene and is characterized by an intact complement system, and wherein the genetically modified immunodeficient NOD mouse has an IL2 receptor gamma chain deficiency and a recombination activating gene 2 deficiency; administering xenograft tumor cells to the genetically modified immunodeficient NOD mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a genetically modified immunodeficient NOD mouse wherein the genome of the genetically modified immunodeficient NOD mouse is homozygous for a Rag2 mutation and wherein the genome of the genetically modified immunodeficient NOD mouse includes a repaired C5 complement component structural gene such that the genetically modified immunodeficient NOD mouse expresses the C5 complement component structural gene and is characterized by an intact complement system, and wherein the mouse has an IL2 receptor gamma chain deficiency and a recombination activating gene 2 deficiency; administering xenograft tumor cells to the genetically modified immunodeficient NOD mouse; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a NSG-Hc$^1$ mouse wherein the genome of the NSG-Hc$^1$ mouse includes a repaired C5 complement component structural gene such that the NSG-Hc$^1$ mouse expresses the C5 complement component structural gene and is characterized by an intact complement system; administering xenograft tumor cells to the NSG-Hc$^1$ mouse wherein the genome of the NSG-Hc$^1$ mouse includes a repaired C5 complement component structural gene such that the NSG-Hc$^1$ mouse expresses the C5 complement component structural gene and is characterized by an intact complement system; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a NRG-Hc$^1$ mouse wherein the genome of the NRG-Hc$^1$ mouse includes a repaired C5 complement component structural gene such that the NRG-Hc$^1$ mouse expresses the C5 complement component structural gene and is characterized by an intact complement system; administering xenograft tumor cells to the NRG-Hc$^1$ mouse wherein the genome of the NRG-Hc$^1$ mouse includes a repaired C5 complement component structural gene such that the NRG-Hc$^1$ mouse expresses the C5 complement component structural gene and is characterized by an intact complement system; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

Methods for producing a mouse model system for assessment of an anti-cancer therapeutic or putative anti-cancer therapeutic are provided according to aspects of the present invention which include providing a NOG-Hc$^1$ mouse wherein the genome of the NOG-Hc$^1$ mouse includes a repaired C5 complement component structural gene such that the NOG-Hc$^1$ mouse expresses the C5 complement component structural gene and is characterized by an intact complement system; administering xenograft tumor cells to the NOG-Hc$^1$ mouse wherein the genome of the NOG-Hc$^1$ mouse includes a repaired C5 complement component structural gene such that the NOG-Hc$^1$ mouse expresses the C5 complement component structural gene and is characterized by an intact complement system; administering an anti-cancer therapeutic antibody or putative anti-cancer therapeutic antibody to the mouse; and assaying a response of the xenograft tumor cells to the anti-cancer therapeutic antibody or putative anti-cancer therapeutic antibody.

According to aspects of the present invention, the xenograft tumor cells administered in the methods for producing a mouse model system for assessment of an anti-cancer therapeutic or putative anti-cancer therapeutic are human xenograft tumor cells.

According to aspects of the present invention, the xenograft tumor cells administered in the methods for producing a mouse model system for assessment of an anti-cancer therapeutic or putative anti-cancer therapeutic are xenograft tumor cells of a cell line.

DETAILED DESCRIPTION OF THE INVENTION

Figure 1A:
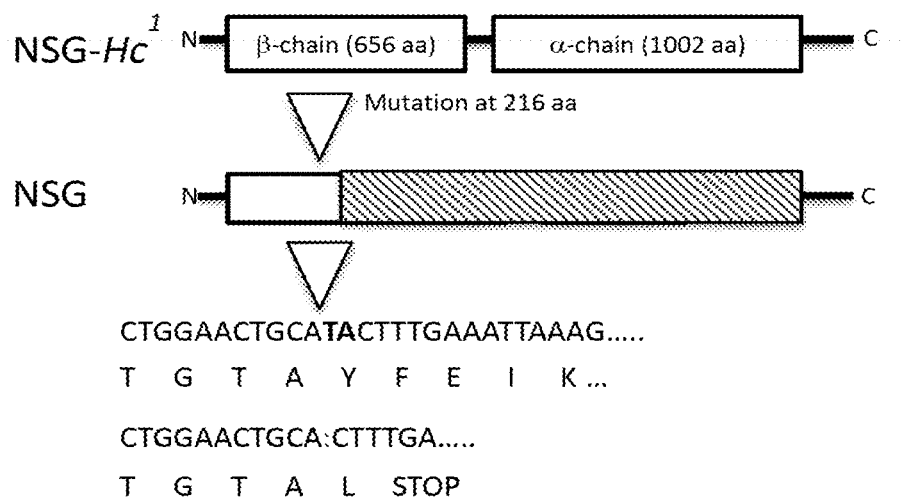
FIG. 1A is a diagram of the mouse C5 complement component structural protein of NSG and NSG-Hc$^1$ mice showing that the 2 base pair deletion in NSG mice results in a premature stop codon and lack of a functional complement system compared to the repaired gene sequence in the NSG-Hc$^{1\ mice}$ which results in production of full-length functional C5. Sequences from top to bottom correspond to SEQ ID Nos: 4-7.

Genetically modified non-human animals, methods and compositions according to aspects of the present invention allow for evaluation of antibody-based therapeutics.

Genetically modified immunodeficient non-human animals are provided by the present invention wherein the genome of the immunodeficient non-human animal includes a repaired C5 complement component structural gene (also known as hemolytic complement, Hc) such that the genetically modified non-human animal expresses the C5 complement component structural gene and is characterized by an intact complement system.

In specific aspects, the present invention relates to immunodeficient non-obese diabetic (NOD), A/J, A/He, AKR, DBA/2, NZB/B1N, B10.D2/oSn and other mouse strains genetically modified to restore complement-dependent cytotoxicity which is lacking in the unmodified immunodeficient mice.

Genetically modified immunodeficient non-obese diabetic mice (NOD) are provided by the present invention wherein the genome of the NOD mouse includes a repaired C5 complement component structural gene such that the genetically modified NOD mouse expresses the C5 complement component structural gene and is characterized by an intact complement system.

Genetically modified immunodeficient NSG mice are provided by the present invention wherein the genome of the NSG mouse includes a repaired C5 complement component structural gene such that the genetically modified NSG mouse expresses the C5 complement component structural gene and is characterized by an intact complement system.

Genetically modified NSG mice with an intact complement system are provided by the present invention, designated NSG-Hc[1] mice.

NSG-Hc[1] mice with an intact complement system and engrafted with cells characterized by abnormal proliferation, such as cancer cells, are provided by the present invention.

Genetically modified immunodeficient NRG mice are provided by the present invention wherein the genome of the NRG mouse includes a repaired C5 complement component structural gene such that the genetically modified NRG mouse expresses the C5 complement component structural gene and is characterized by an intact complement system.

Genetically modified NRG mice with an intact complement system are provided by the present invention, designated NRG-Hc[1] mice.

NRG-Hc[1] mice with an intact complement system and engrafted with cells characterized by abnormal proliferation, such as cancer cells, are provided by the present invention.

Genetically modified immunodeficient NOG mice are provided by the present invention wherein the genome of the NRG mouse includes a repaired C5 complement component structural gene such that the genetically modified NRG mouse expresses the C5 complement component structural gene and is characterized by an intact complement system.

Genetically modified NOG mice with an intact complement system are provided by the present invention, designated NOG-Hc[1] mice.

NOG-Hc[1] mice with an intact complement system and engrafted with cells characterized by abnormal proliferation, such as cancer cells, are provided by the present invention.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W. H. Freeman & Company, 2004; Herdewijn, P. (Ed.), Oligonucleotide Synthesis: Methods and Applications, Methods in Molecular Biology, Humana Press, 2004; A. Nagy, M. Gertsenstein, K. Vintersten, R. Behringer (Eds) 2002, Manipulating the Mouse Embryo: A Laboratory Manual, $3^{rd}$ edition, Cold Spring Harbor Laboratory Press, ISBN-10: 0879695919; and K. Turksen (Ed.), Embryonic stem cells: methods and protocols in Methods Mol Biol. 2002; 185, Humana Press; Current Protocols in Stem Cell Biology, ISBN: 9780470151808.

The singular terms "a," "an," and "the" are not intended to be limiting and include plural referents unless explicitly stated otherwise or the context clearly indicates otherwise.

The terms "immunodeficient mouse" and "immunodeficient non-human animal" refer to a mouse or other non-human animal characterized by one or more of: a lack of functional immune cells, such as T cells and B cells; a DNA repair defect; a defect in the rearrangement of genes encoding antigen-specific receptors on lymphocytes; and a lack of immune functional molecules such as IgM, IgG1, IgG2a, IgG2b, IgG3 and IgA.

Immunodeficient animals, such as mice, can be characterized by one or more deficiencies in a gene involved in immune function, such as Rag1 and Rag2 (Oettinger, M. A et al., Science, 248:1517-1523, 1990; and Schatz, D. G. et al., Cell, 59:1035-1048, 1989)

The term "recombination activating gene 1 deficiency" refers to decreased RAG 1 compared to a wild-type non-human animal. RAG 1 is an enzyme functional in the rearrangement and recombination of the genes encoding immunoglobulin and T cell receptor molecules and deficiency reduces or eliminates generation of mature T and B cells. Decreased RAG 1 can be due to gene deletion or mutation. Decreased RAG 1 can be detected, for example, by detection of RAG 1 gene deletion or mutation and/or detection of decreased RAG 1 expression using well-known methods.

The term "recombination activating gene 2 deficiency" refers to decreased RAG 2 compared to a wild-type non-human animal. RAG 2 is an enzyme functional in the rearrangement and recombination of the genes encoding immunoglobulin and T cell receptor molecules and deficiency reduces or eliminates generation of mature T and B cells. Decreased RAG 2 can be due to gene deletion or mutation. Decreased RAG 2 can be detected, for example, by detection of RAG 2 gene deletion or mutation and/or detection of decreased RAG 2 expression using well-known methods.

Immunodeficient mice may have any of these or other defects which result in abnormal immune function in the mice.

Particularly useful immunodeficient mouse strains are NOD.Cg-Prkdc$^{scid}$ $Il2rg^{tm1Wjl}$/SzJ, commonly referred to as NOD scid gamma (NSG) mice, described in detail in Shultz L D et al, 2005, J. Immunol, 174:6477-89; NOD.Cg-Rag1$^{tm1Mom}$ Il2rg$^{tm1Wjl}$/SzJ, Shultz L D et al, 2008, Clin Exp Immunol 154(2):270-84 commonly referred to as NRG mice; and NOD.Cg-Prkdc$^{scid}$ Il2rg$^{tm1Sug}$/JicTac, commonly referred to as NOG mice, described in detail in Ito, M. et al., Blood 100, 3175-3182 (2002).

The term "severe combined immune deficiency (SCID)" refers to a condition characterized by absence of T cells and lack of B cell function.

Common forms of SCID include: X-linked SCID which is characterized by gamma chain gene mutations in the IL2RG gene and the lymphocyte phenotype T(−) B(+) NK(−); and autosomal recessive SCID characterized by Jak3 gene mutations and the lymphocyte phenotype T(−) B(+) NK(−), ADA gene mutations and the lymphocyte phenotype T(−) B(−) NK(−), IL-7R alpha-chain mutations and the lymphocyte phenotype T(−) B(+) NK(+), CD3 delta or epsilon mutations and the lymphocyte phenotype T(−) B(+) NK(+), RAG1/RAG2 mutations and the lymphocyte phenotype T(−) B(−) NK(+), Artemis gene mutations and the lymphocyte phenotype T(−) B(−) NK(+), CD45 gene mutations and the lymphocyte phenotype T(−) B(+) NK(+).

A genetically modified mouse according to aspects of the present invention has the severe combined immunodeficiency mutation (Prkdc$^{scid}$), commonly referred to as the scid mutation. The scid mutation is well-known and located on mouse chromosome 16 as described in Bosma, et al., Immunogenetics 29:54-56, 1989. Mice homozygous for the scid mutation are characterized by an absence of functional T cells and B cells, lymphopenia, hypoglobulinemia and a normal hematopoetic microenvironment. The scid mutation can be detected, for example, by detection of markers for the scid mutation using well-known methods, such as PCR or flow cyotometry.

A genetically modified immunodeficient mouse according to aspects of the present invention has an IL2 receptor gamma chain deficiency. The term "IL2 receptor gamma chain deficiency" refers to decreased IL2 receptor gamma chain. Decreased IL2 receptor gamma chain can be due to gene deletion or mutation. Decreased IL2 receptor gamma chain can be detected, for example, by detection of IL2 receptor gamma chain gene deletion or mutation and/or detection of decreased IL2 receptor gamma chain expression using well-known methods.

The terms "NOD scid gamma" and "NSG" are used interchangeably herein to refer to a well-known immunodeficient mouse strain NOD.Cg-Prkdc$^{scid}$ $^{Il}$2rg$^{tm1Wjl}$/SzJ. NSG mice combine multiple immune deficits from the NOD/ShiLtJ background, the severe combined immune deficiency (scid) mutation, and a complete knockout of the interleukin-2 receptor gamma chain. As a result, NSG mice lack mature T, B and NK cells, and are deficient in cytokine signaling. NSG mice are characterized by lack of IL2R-γ (gamma c) expression, no detectable serum immunoglobulin, no hemolytic complement, no mature T lymphocytes, and no mature natural killer cells.

The term "NRG" is used herein to refer to a well-known immunodeficient mouse strain NOD.Cg-Rag1$^{tm1Mom}$Il2rg$^{tm1Wjl}$/SzJ. NRG mice combine multiple immune deficits from the NOD/ShiLtJ background, a complete knockout of Rag1 due to the Rag1$^{tm1Mom}$ mutation and a complete knockout of the interleukin-2 receptor gamma chain. As a result, NRG mice lack mature T, B and NK cells, and are deficient in cytokine signaling. NRG mice are characterized by lack of IL2R-γ (gamma c) expression, no detectable serum immunoglobulin, no hemolytic complement, no mature T lymphocytes, and no mature natural killer cells.

The term "NOG" is used herein to refer to a well-known immunodeficient mouse strain NOD.Cg-Prkdc$^{scid}$ Il2rg$^{tm1Sug}$/JicTac. NOG mice combine multiple immune deficits from the NOD/Shi background, the severe combined immune deficiency (scid) mutation, and a complete knockout of the interleukin-2 receptor gamma chain function. As a result, NOG mice lack mature T, B and NK cells, and are deficient in cytokine signaling. NOG mice are characterized by a truncation mutation of IL2R-γ (gamma c) such that ligands can still bind to the truncated protein but no signal is generated, no detectable serum immunoglobulin, no hemolytic complement, no mature T lymphocytes, and no mature natural killer cells.

Genetically modified NOD mice are provided by the present invention wherein the genome of the mouse comprises a repaired C5 complement component structural gene such that the genetically modified NOD mouse expresses the C5 complement component structural gene and is characterized by an intact complement system. Such genetically modified NOD mice, NOD-Hc$^1$, are useful for combining with immunodeficient mice, such as by mating or by in vitro or other in vivo techniques for producing genetically modified immunodeficient mice such as described herein.

The terms "express," "expression," "expressing" and "expresses" with reference to the C5 complement component structural gene refers to transcription of the C5 complement component structural gene to produce a corresponding mRNA and/or translation of the mRNA to produce a functional corresponding the C5 complement component structural protein.

The C5 complement component structural gene and corresponding protein are well-known. *Mus musculus* C5 complement component structural protein is shown as SEQ ID NO: 1 herein.

A 2-base pair (TA) deletion in the C5 complement component structural gene is responsible for the lack of C5 protein expression in NOD mice (including NSG, NRG and NOG strains) as described in Baxter, A. G. et al., Diabetes, 42(11):1574-8, 1993 as well as in A/J, A/He, AKR, DBA/2, NZB/B1N and B10.D2/oSn mouse strains. This deletion close to the 5' end of exon 7 in the c5 gene located on chromosome 2 generates a premature stop codon and prevents expression of C5.

Thus, a repaired C5 complement component structural gene restores expression of the C5 complement component structural gene such that C5 complement component structural protein is produced and the genetically modified mice are characterized by an intact complement system.

The repaired C5 complement component structural gene is preferably repaired to replace the missing 2 base-pair deletion such that the repaired gene encodes the wild-type protein sequence of SEQ ID NO:1.

Any of various methods can be used to repair the C5 complement component structural gene in a mouse having a mutant C5 complement component structural gene to produce a genetically modified immunodeficient mouse whose genome includes a repaired C5 complement component structural gene. The C5 complement component structural gene is repaired in the genome of genetically modified animals according to standard methods of genetic engineering such as, but not limited to, gene editing methods, homologous recombination and transgenic expression of antisense RNA. Such techniques are well-known in the art and further include, but are not limited to, pronuclear microinjection and transformation of embryonic stem cells. Methods for generating genetically modified animals whose genome includes a repaired C5 complement component structural gene include, but are not limited to, those described in J. P. Sundberg and T. Ichiki, Eds., Genetically Engineered Mice Handbook, CRC Press; 2006; M. H. Hofker and J. van Deursen, Eds., Transgenic Mouse Methods and Protocols, Humana Press, 2002; A. L. Joyner, Gene Targeting: A Practical Approach, Oxford University Press, 2000; Manipulating the Mouse Embryo: A Laboratory Manual, 3rd edition, CSH Press; Dec. 15, 2002, ISBN-10: 0879695919; Kursad Turksen (Ed.), Embryonic stem cells: methods and protocols in Methods Mol Biol. 2002; 185, Humana Press; Current Protocols in Stem Cell Biology, ISBN: 978047015180; Meyer et al. PNAS USA, vol. 107 (34), 15022-15026; and CRISPR-Cas: A Laboratory Manual, Jennifer Doudna, J. and Mali, P. (Eds.), CSH Press, 2016, ISBN 978-1-621821-30-4

Generation of a genetically modified immunodeficient non-human animal whose genome includes a repaired C5 complement component structural gene can be achieved by introduction of a gene targeting vector into a preimplantation embryo or stem cells, such as embryonic stem (ES) cells or induced pluripotent stem (iPS) cells.

The term "gene targeting vector" refers to a double-stranded recombinant DNA molecule effective to recombine with and mutate a specific chromosomal locus, such as by insertion into or replacement of the targeted gene.

For targeted gene repair, a gene targeting vector is made using recombinant DNA techniques and includes 5' and 3' sequences which are homologous to the stem cell endogenous C5 complement component structural gene. The gene targeting vector optionally and preferably further includes a selectable marker such as neomycin phosphotransferase, hygromycin or puromycin. Those of ordinary skill in the art are capable of selecting sequences for inclusion in a gene targeting vector and using these with no more than routine experimentation. Gene targeting vectors can be generated recombinantly or synthetically using well-known methodology.

For methods of DNA injection of a gene targeting vector into a preimplantation embryo, the gene targeting vector is linearized before injection into non-human preimplantation embryos. Preferably, the gene targeting vector is injected into fertilized oocytes. Fertilized oocytes are collected from superovulated females the day after mating (0.5 dpc) and injected with the expression construct. The injected oocytes are either cultured overnight or transferred directly into oviducts of 0.5-day p.c. pseudopregnant females. Methods for superovulation, harvesting of oocytes, gene targeting vector injection and embryo transfer are known in the art and described in Manipulating the Mouse Embryo: A Laboratory Manual, 3rd edition, Cold Spring Harbor Laboratory Press; Dec. 15, 2002, ISBN-10: 0879695919. Offspring can be tested for the presence of a repaired C5 complement component structural gene by DNA analysis, such as PCR, Southern blot or sequencing. Mice having a repaired C5 complement component structural gene can be tested for C5 complement component structural protein expression such as by using ELISA or Western blot analysis and/or mRNA expression such as by RT-PCR.

Alternatively the gene targeting vector may be transfected into stem cells (ES cells or iPS cells) using well-known methods, such as electroporation, calcium-phosphate precipitation and lipofection.

Mouse ES cells are grown in media optimized for the particular line. Typically ES media contains 15% fetal bovine serum (FBS) or synthetic or semi-synthetic equivalents, 2 mM glutamine, 1 mM Na Pyruvate, 0.1 mM non-essential amino acids, 50 U/ml penicillin and streptomycin, 0.1 mM 2-mercaptoethanol and 1000 U/ml LIF (plus, for some cell lines chemical inhibitors of differentiation) in Dulbecco's Modified Eagle Media (DMEM). A detailed description is known in the art (Tremml et al., 2008, Current Protocols in Stem Cell Biology, Chapter 1:Unit 1C.4. For review of inhibitors of ES cell differentiation, see Buehr, M., et al. (2003). Genesis of embryonic stem cells. Philosophical Transactions of the Royal Society B: Biological Sciences 358, 1397-1402.

The cells are screened for a repaired C5 complement component structural gene by DNA analysis, such as PCR, Southern blot or sequencing. Cells with the correct homologous recombination event repairing the C5 complement component structural gene can be tested for C5 complement component structural protein expression such as by using ELISA or Western blot analysis and/or mRNA expression such as by RT-PCR. If desired, the selectable marker can be removed by treating the stem cells with Cre recombinase. After Cre recombinase treatment the cells are analyzed for the presence of the nucleic acid encoding C5 complement component structural protein.

Selected stem cells with the correct genomic event repairing the C5 complement component structural gene can be injected into preimplantation embryos. For microinjection, ES or iPS cell are rendered to single cells using a mixture of trypsin and EDTA, followed by resuspension in ES media. Groups of single cells are selected using a finely drawn-out glass needle (20-25 micrometer inside diameter) and introduced through the embryo's zona pellucida and into the blastocysts cavity (blastocoel) using an inverted microscope fitted with micromanipulators. Alternatively to blastocyst injection, stem cells can be injected into early stage embryos (e.g. 2-cell, 4-cell, 8-cell, premorula or morula). Injection may be assisted with a laser or piezo pulses drilled opening the zona pellucida. Approximately 9-10 selected stem cells (ES or iPS cells) are injected per blastocysts, or 8-cell stage embryo, 6-9 stem cells per 4-cell stage embryo, and about 6 stem cells per 2-cell stage embryo. Following stem cell introduction, embryos are allowed to recover for a few hours at 37° C. in 5% CO2, 5% 02 in nitrogen or cultured overnight before transfer into pseudopregnant recipient females. In a further alternative to stem cell injection, stem cells can be aggregated with morula stage embryos. All these methods are well established and can be used to produce stem cell chimeras. For a more detailed description see Manipulating the Mouse Embryo: A Laboratory Manual, 3rd edition (A. Nagy, M. Gertsenstein, K. Vintersten, R. Behringer, Cold Spring Harbor Laboratory Press; Dec. 15, 2002, ISBN-10: 0879695919, Nagy et al., 1990, Development 110, 815-821; U.S. Pat. No. 7,576,259: Method for making genetic modifications, U.S. Pat. Nos. 7,659,442, 7,294,754, Kraus et al. 2010, Genesis 48, 394-399).

Clustered Regularly Interspaced Short Palindromic Repeats (CRISPR) and CRISPR-associated (Cas) systems can be used to repair the C5 complement component structural gene in non-human animals, including mice (e.g. NSG or NRG mice). Three types (I-III) of CRISPR systems have been identified across a wide range of bacterial and archaeal hosts, wherein each system comprises a cluster of CRISPR-associated (Cas) genes, noncoding RNAs and a distinctive array of repetitive elements (direct repeats). These direct repeats are interspaced by short variable sequences derived from exogenous DNA targets known as protospacers, and together they constitute the CRISPR RNA (crRNA) array.

Within the DNA target, each protospacer is associated with a protospacer adjacent motif (PAM), which can vary depending on the specific CRISPR system.

For example, the type II CRISPR-Cas9 system, permits targeted gene cleavage and gene editing in a variety of eukaryotic cells. In order to easily manipulate genes using a CRISPR-Cas9 system, naturally-occurring tracrRNA and crRNA are fused into a single, synthetic 'guide RNA' that directs Cas9 to virtually any desired DNA sequence. Thus, because the endonuclease cleavage specificity in CRISPR-Cas9 system is guided by RNA sequences, editing can be directed to virtually any genomic locus by engineering the guide RNA sequence and delivering it along with the Cas endonuclease to the target cell. The synthetic guide RNA hybridizes to a 20-nucleotide DNA sequence and immediately preceding the specific motif recognized by the Cas9. This results in a double-strand break three nucleotides upstream of the recognized motif. The double strand break can initiate homology-directed repair, which can be exploited with the use of an exogenously introduced double-strand or single-strand DNA repair template to correct a mutation in the genome, such as to repair the C5 complement structural gene. Those of ordinary skill in the art are capable of engineering the guide RNA sequence of a Cas system, such as the CRISPR-Cas9 system, to target the C5 complement structural gene of non-human animals, including a mouse (e.g. an NSG or NRG mouse) and use exogenously introduced double-strand or single-strand DNA repair template to repair the C5 complement structural gene.

Pseudopregnant embryo recipients are prepared using methods known in the art. Briefly, fertile female mice between 6-8 weeks of age are mated with vasectomized or sterile males to induce a hormonal state conductive to supporting surgically introduced embryos. At 2.5 days post coitum (dpc) up to 15 of the stem cell containing blastocysts are introduced into the uterine horn very near to the uterus-oviduct junction. For early stage embryos and morula, such embryos are either cultured in vitro into blastocysts or implanted into 0.5 dpc or 1.5 dpc pseudopregnant females according to the embryo stage into the oviduct. Chimeric pups from the implanted embryos are born 16-20 days after the transfer depending on the embryo age at implantation. Chimeric males are selected for breeding. Offspring can be analyzed for transmission of the ES cell genome by coat color and nucleic acid analysis, such as PCR, Southern blot or sequencing. Further the expression of repaired C5 complement component structural gene can be analyzed for C5 complement component structural protein mRNA or protein expression such as by protein analysis, e.g. immunoassay, or functional assays, to confirm repair of the C5 complement component structural gene. Offspring having the repaired C5 complement component structural gene are intercrossed to create non-human animals homozygous for the repaired C5 complement component structural gene. The transgenic mice are crossed to the immunodeficient mice to create a congenic immunodeficient strain with the repaired C5 complement component structural gene.

Methods of assessing a genetically modified non-human animal to determine whether the C5 complement component structural gene is repaired such that the non-human animal expresses the repaired C5 complement component structural gene are well-known and include standard techniques such as nucleic acid assays, spectrometric assays, immunoassays and functional assays.

One or more standards can be used to allow quantitative determination of C5 complement component structural protein in a sample.

Assays for assessment of function repaired C5 complement component structural gene in an animal having a putative repair of the C5 complement component structural gene can be performed.

Optionally, genetically modified immunodeficient non-human animals characterized by repaired C5 complement component structural gene of the present invention are produced by selective breeding. A first parental strain of non-human animal which has a first desired genotype may be bred with a second parental strain of non-human animal which has a second desired genotype to produce offspring which are genetically modified non-human animals having the first and second desired genotypes. For example, a first mouse which is immunodeficient and has a mutated C5 complement component structural gene may be bred with a second mouse which has an intact C5 complement component structural gene and further genetically crossed to produce offspring which are immunodeficient and have a repaired C5 complement component structural gene such that the C5 complement component structural gene is expressed and the animal has an intact complement system and demonstrates complement-dependent cytotoxicity.

In further examples, an NSG, NRG or NOG mouse may be bred with a mouse which has an intact C5 complement component structural gene to produce offspring which are immunodeficient and have a repaired C5 complement component structural gene such that the produced mice have an intact complement system and demonstrate complement-dependent cytotoxicity.

Aspects of the invention provide genetically modified animals that include a repaired C5 complement component structural gene in substantially all of their cells, as well as genetically modified animals that include a repaired C5 complement component structural gene in some, but not all their cells.

Genetically modified immunodeficient non-human animals of the present invention are preferably non-human mammals, particularly rodents, such as mice, rats or guinea pigs.

Methods for producing a non-human animal model system for response of xenograft tumor cells according to aspects of the present invention include providing a genetically modified immunodeficient non-human animal comprising a repaired C5 complement component structural gene such that the genetically modified immunodeficient non-human animal expresses C5 complement component structural protein and has a functioning complement system; and administering xenograft tumor cells to the genetically modified immunodeficient non-human animal. The immunodeficient non-human animal may have a severe combined immunodeficiency, an IL2 receptor gamma chain deficiency, or a severe combined immunodeficiency and an IL2 receptor gamma chain deficiency in combination.

The term "xenograft" is used herein with reference to a host cell or organism to indicate that the material referred to as "xenograft" is derived from another species than that of the host cell or organism.

The term "tumor cells" as used herein refers to abnormally proliferating cells, such as cancer cells.

Methods for producing a mouse model system for response of xenogeneic tumor cells according to aspects of the present invention include providing a genetically modified immunodeficient mouse having a repaired C5 complement component structural gene such that the genetically modified immunodeficient mouse expresses C5 complement component structural protein and has a functioning complement system; and administering xenogeneic tumor cells to the genetically modified immunodeficient mouse. The immunodeficient mouse may have a severe combined immunodeficiency, an IL2 receptor gamma chain deficiency, or a severe combined immunodeficiency and an IL2 receptor gamma chain deficiency in combination.

Tumor cells for administration to a genetically modified immunodeficient animal having a repaired C5 complement component structural gene can be obtained from a tumor biopsy or necropsy sample from a subject or a cancer cell line.

Administration of tumor cells to an animal for xenograft is well known, such as, but not limited to, subcutaneous surgical insertion of tumor cells or tumor tissue, or subcutaneous or intravenous injection of tumor cells or tumor tissue, see for example, Morton et al., Nature Protocols 2, 247-250 (2007); and Fujii et al., Pathol. Int., 2008, 58(9): 559-67.

Engraftment of xenograft tumor cells can be assessed by any of various methods, such as, but not limited to, optical inspection of tumor growth, blood sampling and analysis where the tumor cells are not solid tumor forming cells, and imaging of the animal such as MRI, PET, CT or fluorescent imaging.

Exemplary methods for isolation of xenograft tumor cells, administration of the xenograft tumor cells to a host organism and methods for assessing engraftment thereof are well known.

The number of xenograft tumor cells administered to the recipient animal to be engrafted is not limited and can be in the range of 1 cell-1 billion cells, such as 1 cell-500 million cells, 1 cell-100 million cells, 1 cell-10 million cells, 1 cell-5 million cells, 1 cell-1 million cells, 1 cell-500,000 cells, 1 cell-100,000 cells, 1 cell-50,000 cells, 1 cell-10,000 cells or 1 cell-1,000 cells, of such cells.

Methods are provided according to aspects of the present invention which include administration of an anti-cancer therapeutic to the xenograft tumor cells in an immunodeficient animal having a repaired C5 complement component structural gene and analysis of the effect of the anti-cancer therapeutic on the xenograft tumor cells.

Assays for evaluation of C5 complement component structural gene defects and repair Binding assays are optionally used in assays according to aspects of the present invention to evaluate C5 complement component structural gene defects and repair.

The term "binding partner" refers to a biological molecule capable of specific binding to a target analyte. Non-limiting examples of binding partners include antibodies, aptamers, receptors, ligands and substrates for enzymatic action of a target analyte. Binding partners may also be nucleic acid probes. The skilled artisan can routinely identify, isolate and/or make binding partners and use them in binding assays. Such techniques are well-known to those of ordinary skill in the art.

A binding assay can be performed according to any of various methods that allow for detection of one or more target analytes by binding to a binding partner. Binding of a target analyte and binding agent can be detected directly or indirectly, such as by use of detectable labels.

Nucleic acid assays such as sequencing, an amplification assay and/or a hybridization assay can be used to detect expression of a target analyte. Nucleic acid assays, include, but are not limited to, amplification reactions such as polymerase chain reactions (PCR), such as RT-PCR; dot blot; in situ hybridization; Northern blot; and RNase protection. Details of such assays are described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002, for example.

A nucleic acid probe or primer able to hybridize to a target analyte mRNA or cDNA to detect and/or quantify mRNA or cDNA can be used in a nucleic assay. A nucleic acid probe can be an oligonucleotide of at least 10, 15, 30, 50 or 100 nucleotides in length and sufficient to specifically hybridize under stringent conditions to a target mRNA or cDNA or complementary sequence thereof. A nucleic acid primer can be an oligonucleotide of at least 10, 15 or 20 nucleotides in length and sufficient to specifically hybridize under stringent conditions to the mRNA or cDNA, or complementary sequence thereof. The terms "specific hybridization" and "specifically hybridizes" refer to hybridization of a particular nucleic acid to a target nucleic acid without substantial hybridization to nucleic acids other than the target nucleic acid in a sample.

Stringency of hybridization and washing conditions depends on several factors, including the Tm of the probe and target and ionic strength of the hybridization and wash conditions, as is well-known to the skilled artisan. Hybridization and conditions to achieve a desired hybridization stringency are described, for example, in Sambrook et al., Molecular Cloning: A Laboratory Manual, Cold Spring Harbor Laboratory Press, 2001; and Ausubel, F. et al., (Eds.), Short Protocols in Molecular Biology, Wiley, 2002.

A sample from a non-human animal is optionally purified for assay according to a method of the present invention. Methods for isolation of mRNA and/or generation of cDNA for use in an assay of particular sequences are well known in the art.

The term "nucleic acid" refers to RNA or DNA molecules having more than one nucleotide in any form including single-stranded, double-stranded, oligonucleotide or polynucleotide. The term "nucleotide sequence" refers to the ordering of nucleotides in an oligonucleotide or polynucleotide in a single-stranded form of nucleic acid.

The term "amplification assay" refers to a method for copying a template nucleic acid, thereby producing nucleic acids which include copies of all or a portion of the template nucleic acid.

Amplification assays include those which include template directed primer extension catalyzed by a nucleic acid polymerase using a pair of primers which flank the target nucleic acid, illustratively including, but not limited to, polymerase chain reaction (PCR), reverse-transcription PCR (RT-PCR), ligation-mediated PCR (LM-PCR), phi-29 PCR, and other nucleic acid amplification methods, for instance, as described in C. W. Dieffenbach et al., PCR Primer: A Laboratory Manual, Cold Spring Harbor Laboratory Press, 2003; and V. Demidov et al., DNA Amplification: Current Technologies and Applications, Taylor & Francis, 2004. The term "primer" refers to a single stranded oligonucleotide, typically about 9-60 nucleotides in length, that may be longer or shorter, and that serves as a point of initiation for template-directed DNA synthesis.

Appropriate reactions conditions for in vitro nucleic acid amplification methods include presence of suitable reaction components including, but not limited to, a polymerase and nucleotide triphosphates. One of skill in the art will be able to determine conditions suitable for amplification of the target nucleic acids with only routine experimentation using primers of the present invention including choice of factors such as buffer, nucleotides, pH, Mg salt concentration, primer concentration and temperature. The nucleic acid product of the amplification methods optionally contains additional materials such as, but not limited to, non-target nucleic acid sequences, functional groups for chemical reaction and detectable labels, present in the primers and not present in the original DNA template. PCR may also being performed as quantitative PCR (Q-PCR) also known as real-time PCR or kinetic PCR (KPCR). Q-PCR is used to amplify and simultaneously quantify a targeted DNA molecule.

The terms "quantitative PCR" or "Q-PCR" refer to a variety of methods for quantifying the results of polymerase chain reactions. Q-PCR methods generally determine or compare the amplification factor, such as determining the threshold cycle (Ct), or are co-amplification methods that compare the amount of produce generated from simultaneous amplification of target and standard templates. Many Q-PCR techniques include reporter probes, intercalator dyes or both. Reporter probes include, but are not limited to, TaqMan® probes (Applied Biosystems), molecular beacons, Scorpion® primers, Lux™ primers and FRET primers; and intercalator dyes include, but are not limited to, ethidium bromide, SYBR® Green I (Molecular Probes) and PicoGreen® (Molecular Probes).

For one or more specific sequences in a DNA sample, Real Time-PCR enables both detection and quantification. The quantity can be either an absolute number of copies or a relative amount when normalized to DNA input or additional normalizing genes. Two common methods for detection of products in real-time PCR are: (1) non-specific fluorescent dyes that intercalate with any double-stranded DNA, and (2) sequence-specific DNA probes consisting of oligonucleotides that are labeled with a fluorescent reporter which permits detection only after hybridization of the probe with its complementary DNA target. For example TaqMan probes are used. The TaqMan probe principle relies on the 5'-3' exonuclease activity of Taq polymerase to cleave a dual-labeled probe during hybridization to the complementary target sequence and fluorophore-based detection. As in other real-time PCR methods, the resulting fluorescence signal permits quantitative measurements of the accumulation of the product during the exponential stages of the PCR; however, the TaqMan probe significantly increases the specificity of the detection. TaqMan probes consist of a fluorophore covalently attached to the 5'-end of the oligonucleotide probe and a quencher at the 3'-end. Several different fluorophores (e.g. 6-carboxyfluorescein, acronym: FAM, or tetrachlorofluorescin, acronym: TET) and quenchers (e.g. tetramethylrhodamine, acronym: TAMRA, or dihydrocyclopyrroloindole tripeptide minor groove binder, acronym: MGB) are available. The quencher molecule quenches the fluorescence emitted by the fluorophore when excited by the cycler's light source via FRET (Fluorescence Resonance Energy Transfer) As long as the fluorophore and the quencher are in proximity, quenching inhibits any fluorescence signals.

TaqMan probes are designed such that they anneal within a DNA region amplified by a specific set of primers. As the Taq polymerase extends the primer and synthesizes the nascent strand (again, on a single-strand template, but in the direction opposite to that shown in the diagram, i.e. from 3' to 5' of the complementary strand), the 5' to 3' exonuclease activity of the polymerase degrades the probe that has annealed to the template. Degradation of the probe releases the fluorophore from it and breaks the close proximity to the quencher, thus relieving the quenching effect and allowing fluorescence of the fluorophore. Hence, fluorescence detected in the real-time PCR thermal cycler is directly proportional to the fluorophore released and the amount of DNA template present in the PCR.

Hybridization assays for a nucleic acid target include, but are not limited to, dot blot, nucleic acid hybridization, bead assays, in situ hybridization, Northern blot, Southern blot and microarray assays. Details of such assays are described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002, for example.

Nucleic acid hybridization assays include use of a nucleic acid probe which specifically hybridizes to a target nucleic acid under defined hybridization and wash conditions. The term "probe" encompasses nucleic acid sequences of various lengths, typically at least about 9 to about 8000 nucleotides in length, but may be shorter or longer as long as the probe is capable of specifically hybridizing to a target nucleic acid in a nucleic acid hybridization assay. A probe may be single or double stranded and may be generated by recombinant methods, chemical synthesis, isolation from natural sources, or a combination of two or more of these.

Immunoassay methods can be used to assay a target analyte, including, but not limited to, enzyme-linked immunosorbent assay (ELISA), enzyme-linked immunofiltration assay (ELIFA), flow cytometry, immunoblot, immunoprecipitation, immunohistochemistry, immunocytochemistry, luminescent immunoassay (LIA), fluorescent immunoassay (FIA), and radioimmunoassay. Assay methods may be used to obtain qualitative and/or quantitative results. Specific details of suitable assay methods for both qualitative and quantitative assay of a sample are described in standard references, illustratively including E. Harlow and D. Lane, Antibodies: A Laboratory Manual, Cold Spring Harbor Laboratory Press, 1988; F. Breitling and S. Dübel, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; B. K. C. Lo, Antibody Engineering: Methods and Protocols, Methods in Molecular Biology, Humana Press, 2003; F. M. Ausubel et al., Eds., Short Protocols in Molecular Biology, Current Protocols, Wiley, 2002; S. Klussman, Ed., The Aptamer Handbook: Functional Oligonucleotides and Their Applications, Wiley, 2006; Ormerod, M. G., Flow Cytometry: a practical approach, Oxford University Press, 2000; Givan, A. L., Flow Cytometry: first principles, Wiley, New York, 2001; Gorczyca, W., Flow Cytometry in Neoplastic Hematology: morphologic-immunophenotypic correlation, Taylor & Francis, 2006; Crowther, J. R., The ELISA Guidebook (Methods in Molecular Biology), Humana Press, 2000; Wild, D., The Immunoassay Handbook, 3rd Edition, Elsevier Science, 2005; and J. Sambrook and D. W. Russell, Molecular Cloning: A Laboratory Manual, Cold Spring Harbor Laboratory Press, 3rd Ed., 2001.

Antibodies and methods for preparation of antibodies are well-known in the art. As used herein, the terms "antibody" and "antibodies" encompass monoclonal antibodies, polyclonal antibodies, bispecific antibodies, multispecific antibodies, human antibodies, humanized antibodies, chimeric antibodies, camelized antibodies, single domain antibodies, single-chain Fvs (scFv), single chain antibodies, disulfide-linked Fvs (sdFv), and anti-idiotypic (anti-Id) antibodies and antigen-binding fragments of any of the above. In particular, antibodies include immunoglobulin molecules and immunologically active fragments of immunoglobulin molecules, i.e., molecules that contain an antigen binding site. Immunoglobulin molecules are of any type (e.g., IgG, IgE, IgM, IgD, IgA and IgY), class (e.g., IgG1, IgG2, IgG3, IgG4, IgA1 and IgA2), or subclass.

As used herein, the terms "antibody fragment" and "antigen-binding fragment" defines a fragment of an antibody that immunospecifically binds to a target analyte. Antibody fragments may be generated by any technique known to one of skill in the art. For example, Fab and F(ab')2 fragments may be produced by proteolytic cleavage of immunoglobulin molecules, using enzymes such as papain (to produce Fab fragments) or pepsin (to produce F(ab')2 fragments). Antibody fragments are also produced by recombinant DNA technologies.

Antibodies, antigen-binding fragments, methods for their generation and methods for screening of generated antibodies for substantially specific binding to an antigen are known in the art and such antibodies, antigen binding fragments and methods are described in further detail, for instance, in Antibody Engineering, Kontermann, R. and Dübel, S. (Eds.), Springer, 2001; Harlow, E. and Lane, D., Antibodies: A Laboratory Manual, Cold Spring Harbor Laboratory Press, 1988; F. Breitling and S. Dübel, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; Ausubel, F. et al., (Eds.), Short Protocols in Molecular Biology, Wiley, 2002; J. D. Pound (Ed.) Immunochemical Protocols, Methods in Molecular Biology, Humana Press, 2nd ed., 1998; B. K. C. Lo (Ed.), Antibody Engineering: Methods and Protocols, Methods in Molecular Biology, Humana Press, 2003; and Kohler, G. and Milstein, C., Nature, 256:495-497 (1975). Antibodies for target analytes can be produced in animals, synthesized, produced by recombinant methods and/or obtained commercially.

Aptamers can be used to assay a target analyte. The term "aptamer" refers to a peptide and/or nucleic acid that substantially specifically binds to a specified substance. In the case of a nucleic acid aptamer, the aptamer is characterized by binding interaction with a target other than Watson/Crick base pairing or triple helix binding with a second and/or third nucleic acid. Such binding interaction may include Van der Waals interaction, hydrophobic interaction, hydrogen bonding and/or electrostatic interactions, for example. Similarly, peptide-based aptamers are characterized by specific binding to a target wherein the aptamer is not a naturally occurring ligand for the target. Techniques for identification and generation of peptide and nucleic acid aptamers and their use are known in the art as described, for example, in F. M. Ausubel et al., Eds., Short Protocols in Molecular Biology, Current Protocols, Wiley, 2002; S. Klussman, Ed., The Aptamer Handbook: Functional Oligonucleotides and Their Applications, Wiley, 2006; and J. Sambrook and D. W. Russell, Molecular Cloning: A Laboratory Manual, Cold Spring Harbor Laboratory Press, 3rd Ed., 2001.

Detecting binding between a target analyte present in a sample and a binding partner is achieved by any of various methods known in the art, illustratively including detection of a detectable label directly or indirectly attached to the target analyte or the binding partner. The term "detectable label" refers to a material capable of producing a signal indicative of the presence of the detectable label by any appropriate method illustratively including spectroscopic, optical, photochemical, biochemical, enzymatic, electrical and/or immunochemical. Examples of detectable labels illustratively include a fluorescent moiety, a chemiluminescent moiety, a bioluminescent moiety, an electron dense particle, a magnetic particle, an enzyme, a substrate, a radioisotope and a chromophore.

The identity of a particular detectable label or labels used depends on the detection process used. Such detection processes are incorporated in particular assay formats illustratively including ELISA, Western blot, immunoprecipitation, immunocytochemistry, immuno-fluorescence assay, liquid chromatography, flow cytometry, other detection processes known in the art, or combinations thereof.

A binding assay can incorporate a binding partner attached to a support. A support with attached binding partner used in a binding assay can be solid or semi-solid and can be any of various materials such as glass, silicon, paper, a synthetic or naturally occurring polymer, such as polystyrene, polycarbonate, polypropylene, PVDF, nylon, cellulose, agarose, dextran, and polyacrylamide or any other material to which a binding partner can be stably attached for use in a binding assay.

A support used can include functional groups for binding to binding partners, such as, but not limited to carboxyl, amine, amino, carboxylate, halide, ester, alcohol, carbamide, aldehyde, chloromethyl, sulfur oxide, nitrogen oxide, epoxy and/or tosyl functional groups. Attachment of binding partners to a support is achieved by any of various methods, illustratively including adsorption and chemical bonding. In one example, 1-Ethyl-3-[3-dimethylaminopropyl]carbodiimide hydrochloride, EDC or EDAC chemistry, can be used to attach binding partners to particles. The binding partners can be bonded directly or indirectly to the material of the support, for example, via bonding to a coating or linker disposed on the support. Functional groups, modification thereof and attachment of a binding partner to a support are known in the art, for example as described in Fitch, R. M., Polymer Colloids: A Comprehensive Introduction, Academic Press, 1997.

Such supports can be in any of a variety of forms and shapes including, but not limited to, microtiter plates, microtiter wells, pins, fibers, beads, slides, silicon chips and membranes such as a nitrocellulose or PVDF membrane.

Any of various spectroscopy methods can be used to assay a target analyte according to aspects of the present invention, including, but not limited to, gas chromatography, liquid chromatography, ion mobility spectrometry, mass spectrometry, liquid chromatography-mass spectrometry (LC-MS or HPLC-MS), ion mobility spectrometry-mass spectrometry, tandem mass spectrometry, gas chromatography-mass spectrometry, matrix-assisted desorption ionization time-of-flight (MALDI-TOF) mass spectrometry, surface-enhanced laser desorption ionization (SELDI) and nuclear magnetic resonance spectroscopy, all of which are well-known to the skill artisan.

Optionally, spectrometric analysis is used to assay a sample for a target analyte. Mass analysis can be used in an assay according to aspects of the present invention. Mass analysis is conducted using, for example, time-of-flight (TOF) mass spectrometry or Fourier transform ion cyclotron resonance mass spectrometry. Mass spectrometry techniques are known in the art and exemplary detailed descriptions of methods for protein and/or peptide assay are found in Li J., et al., Clin Chem., 48(8):1296-304, 2002; Hortin, G. L., Clinical Chemistry 52: 1223-1237, 2006; A. L. Burlingame, et al. (Eds.), Mass Spectrometry in Biology and Medicine, Humana Press, 2000; and D. M. Desiderio, Mass Spectrometry of Peptides, CRC Press, 1990.

Assays for evaluation of effect of an anti-cancer therapeutic antibody or putative anti-cancer therapeutic antibody on xenograft tumor cells.

Assays performed on living animals for evaluation of effect of an anti-cancer therapeutic antibody or putative anti-cancer therapeutic antibody on xenograft tumor cells can be used such as survival studies, measurement of tumor size and animal weight.

Tumor biopsies can be assessed for proliferation and viability of xenograft cells by any of various assays known in the art, such as by staining with trypan blue or propidium iodide.

Analysis of animal tissues and/or blood samples can be performed to determine toxicity of the anti-cancer therapeutic as well as the therapeutic effect of an anti-cancer therapeutic.

Tumor burden and metastasis can be evaluated by any of various methods such as flow cytometry and/or immunohistochemistry.

Binding assays such as those described herein can be used to evaluate the effect of an anti-cancer therapeutic on a xenograft, such as assays to detect one or more tumor biomarkers.

The term "anti-cancer therapeutic antibody" refers to an antibody known to have an anti-cancer effect at least partly mediated by complement dependent cytotoxicity on at least one type of cancer cell. Such antibodies are known in the art and illustratively include rituximab, trastuzumab, alemtuzumab, cetuximab, panitumumab, catumaxomab, and ofatumumab.

The term "putative anti-cancer therapeutic antibody" refers to an antibody for which an anti-cancer effect may be at least partly mediated by complement dependent cytotoxicity on at least one type of cancer cell. Methods for assessing the effect of an anti-cancer therapeutic provided according to aspects of the present invention allow for determination of whether the putative anti-cancer therapeutic antibody has an anti-cancer effect may be at least partly mediated by complement dependent cytotoxicity on at least one type of cancer cell.

An anti-cancer therapeutic antibody or putative anti-cancer therapeutic antibody can be an antibody of any type appropriate for mediating an anti-cancer effect by complement dependent cytotoxicity, illustratively including an antibody derived from any species of animal such as mouse, rat, guinea pig, rabbit, goat, sheep, pig, cow, horse, chicken, dog, camel, human and non-human primate. The anti-cancer therapeutic antibody or putative anti-cancer therapeutic antibody can be any type of antibody capable of mediating an anti-cancer effect by complement dependent cytotoxicity such as a monoclonal antibody, polyclonal antibody, bispecific antibody, multispecific antibody, human antibody, humanized antibody, chimeric antibody, camelized antibody, single domain antibody, single-chain Fvs (scFv), single chain antibody, disulfide-linked Fvs (sdFv), and anti-idiotypic (anti-Id) antibody and fragments of any of the above capable of mediating an anti-cancer effect by complement dependent cytotoxicity. In particular, antibodies include immunoglobulin molecules and immunologically active fragments of immunoglobulin molecules mediating lysis of a target cell, i.e. an anti-cancer effect on a target cancer cell, by complement dependent cytotoxicity. Such antibodies are of any type, e.g., IgG and IgM, class e.g., IgG1, IgG2, IgG3, IgG4, or subclass capable of mediating lysis of a target cell, i.e. an anti-cancer effect on a target cancer cell, by complement dependent cytotoxicity.

Standards

Standards suitable for assays are well-known in the art and the standard used can be any appropriate standard.

In one example, a standard is a result of an assay of the one or more tumor biomarkers in a comparable sample from a control animal.

A standard may be a reference level of the one or more tumor biomarkers previously determined in a sample of an individual control animal or in a population of control animals and stored in a print or electronic medium for recall and comparison to a result of an assay of the one or more tumor biomarkers in an animal to which an anti-cancer therapeutic is administered.

A standard can be an average level of one or more indicators in comparable samples obtained from one or more populations. The "average level" is determined by assay of the one or more indicators in comparable samples obtained from each animal of the population. The term "comparable sample" is used to indicate that the samples are of the same type, i.e. each of the comparable samples is a serum sample, for example.

A difference detected in levels or expression of one or more target analytes in assays of the present invention compared to a standard can be an increase or decrease in level or expression of the one or more target analytes. The magnitude of the increase or decrease can be, for example, at least 5%, 10%, 15%, 20%, 25%, 30%, 35%, 40%, 45%, 50%, 55%, 60%, 65%, 70%, 75%, 80%, 85%, 90%, 95%, 99%, or more, of the standard level.

Assay results can be analyzed using statistical analysis by any of various methods, exemplified by parametric or non-parametric tests, analysis of variance, analysis of covariance, logistic regression for multivariate analysis, Fisher's exact test, the chi-square test, Student's T-test, the Mann-Whitney test, Wilcoxon signed ranks test, McNemar test, Friedman test and Page's L trend test. These and other statistical tests are well-known in the art as detailed in Hicks, CM, Research Methods for Clinical Therapists: Applied Project Design and Analysis, Churchill Livingstone (publisher); 5th Ed., 2009; and Freund, R J et al., Statistical Methods, Academic Press; 3rd Ed., 2010.

Aspects of inventive genetically modified non-human animals, compositions and methods are illustrated in the following examples. These examples are provided for illustrative purposes and are not considered limitations on the scope of inventive compositions and methods.

EXAMPLES

Example 1

Generation of sufficient complement NSG.

Absence of hemolytic complement lytic activity in NOD mice results from a 2 base pair deletion in the Hc gene encoding the C5 complement component. The termination codon UGA is present 4 bp downstream from the deletion that causes the lack of C5 protein expression. The defective $Hc^0$ allele expressed by NOD/Lt mice (Hc locus Chr 2) was replaced by a wild-type $Hc^1$ allele from CBA by outcrossing a CBA/Ls female to a NOD/Lt male mice, followed by ten backcrosses to NOD/Lt mice and fixation of sex chromosomes from NOD/Lt mice. A homozygous congenic mouse strain, designated NOD-$Hc^1$, was obtained carrying Chr 2 alleles derived from CBA/Ls including $Hc^1$ allele, i.e. NOD.CBALs-$Hc^1$/Lt (stock #004306), from The Jackson Laboratory bio-repository. Male NOD.CBALs-$Hc^1$/Lt mice were mated with female NSG mice from the Jackson Laboratory biorepository (stock #005557).

cDNA from F1 offspring mice were subjected to targeted Sanger sequencing capturing up to 0.21 kb region on exon 5 of the Hc gene. The F1 mice were heterozygous for the wild type Hc gene (Hc⁰/Hc¹), the Prkdc$^{scid}$ mutation and the Il2rg$^{null}$ allele. These heterozygous F1 mice were then intercrossed to produce NSG mice homozygous for the Prkdc$^{scid}$, IL2rg$^{tm1Wjl}$ and Hc¹ alleles, i.e. NSG-Hc¹ mice, FIG. 1A. The colony is maintained by sib matings of NSG-Hc¹ mice.

The C5 normal allele to the NSG strain. Primers used were:

```
Primer: Oligonucleotide 947, Oligonucleotide 945

Primer 1 sequence:
                                          (SEQ ID NO: 2)
CAATTAAAGCTTACTATAAGAAGGATTTTACAA Primer 2 sequence:
                                          (SEQ ID NO: 3)
CAAGTTAGATCTAAGCACTAGCTACTCAAACAA
```

Product size: 0.21kb
MGI Accession ID: MGI:6305
212 bp: BALB/cJ, DBA/1J, B10.D2-H2<d>/nSnJ, C57BL/6J
210 bp AKR/J, A/HeJ, B10.D2-H2<d>/oSnJ, NZB/B1NJ, SWR/J, DBA/2.

For Sanger sequencing and genotyping, total genomic DNA was prepared from 2 mm slices of tails of 4-6 week old mice using a 95 degrees 50 mM NaOH heat step followed by neutralization and centrifugation to pellet the debris. A 210 bp product containing exon 5 of the Hc gene was amplified using the following primer set; Forward: CAATTAAAGCTTACTATAAGAAGGATTTTACAA (SEQ ID NO:2) and Reverse: CAAGTTAGATCTAAGCACTAGCTACTCAAACAA (SEQ ID NO:3). Bands of interest were excised and gel extracted using the QIAquick Gel Extraction kit (Qiagen) and eluted in 30 μl double distilled water. If gel extraction was not necessary to separate multiple bands, PCR products were directly cleaned using ExoSAP-It (USB, Cleveland, Ohio). DNA samples were quantitated using the Nanodrop ND-1000 UV spectrophotometer (Nanodrop Technologies, Wilmington, Del.). Sequencing reactions with gene-specific primers were carried out using the BigDye Terminator Cycle Sequencing chemistry and resolved on the AB3703xl (Applied Biosystems Life Technologies, Carlsbad, Calif.). cDNA was sequenced from both strands of NSG and NSG-Hc¹ mice. Sequencher 4.9 (Gene Codes, Ann Arbor, Mich.) was used to assemble DNA sequences.

All mice were reared on NIH 31 M diet and acidified water ad libitum under modified barrier conditions at The Jackson Laboratory in a 12-hr dark/12-hr light cycle.

Example 2

In vitro characterization of complement dependent cytotoxicity in NSG-Hc¹ mice.

Sera from 9-10 month old male BALB/cBy, NSG and NSG-Hc¹ mice were collected and the level of complement activity in mouse sera was determined by examining the capacity of 1:5 diluted mouse sera to lyse antibody coated sheep RBCs, i.e. sensitized cells (EA cells). Sheep RBCs (Cat #10H72) and rabbit antiserum to sheep RBCs (Cat #10K945), were purchased form Grainger. Sheep RBCs (SRBC) were washed and maintained in HBSS medium. Whole mouse blood was collected directly into Becton Dickinson microtainer tubes with serum separator and allowed to clot by leaving undisturbed for 15 minutes at room temperature. The clots were removed by centrifugation and the sera were removed using a sterile pipette. Complement activity in mouse sera was determined by measuring the lysis of antibody-coated SRBC in various serum dilutions. Briefly, SRBC cells incubated with anti-SRBC antibody (EA cells) were prepared by mixing an equal volume of RBCs (1×10⁹ cells/ml) and 1:10 diluted anti-sheep RBC rabbit Ab in HBSS and incubating at 37° C. for 30 min. The complement activity was determined by mixing 25 μl of EA cells at 10⁹/ml in HBSS medium with 175 ul of 1:5 diluted mouse sera in a V-bottom 96 well plate. EA cells incubated either with ACK lysis buffer or only HBSS medium were used as positive and negative controls, respectively. EA cells and sera were incubated for 1 hour at 37° C., centrifuged for 10 min at 2,500×g and the OD 405 of the supernatant measured to assess EA cell lysis. Percentage complement-dependent lysis in mouse sera was calculated relative to cells lysed in ACK lysis buffer (100% lysis) and cells incubated with HBSS only (0% lysis).

Figure 1B:
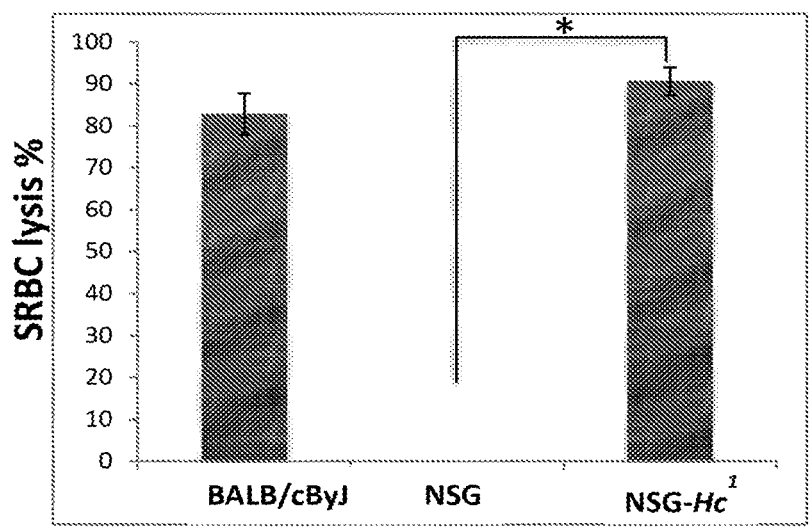
FIG. 1B is a representative graph demonstrating the level of lysis of antibody coated sheep RBCs, i.e sensitized cells (EA cells), when incubated with either a 1:5 diluted sera from age and sex matched NSG or NSG-Hc$^1$ mice. Serum from BALB/cByJ mice was used as a positive control. Data are reported as the mean±SD. *P<0.0001.

Sera from NSG-Hc¹ mice produced similar level lysis of EA cells as sera from BALB/cBy mice carrying wild-type Hc¹ gene, FIG. 1B. However, <0.1% of EA cells lysis was observed when incubated with sera from NSG mice carrying the mutant Hc⁰ allele, FIG. 1B. This result validated that the congenic Hc¹ allele in NSG-Hc¹ mice transcribes a functional C5 protein.

Example 3

In vivo characterization of complement dependent cytotoxicity in NSG-Hc¹ mice.

On day 0 age-matched female NSG and NSG-Hc¹ mice were divided into five groups (5-7 mice in each group) and injected with 1×10⁵ viable Daudi Burkitt's lymphoma cells via the tail vein. Daudi cells were purchased from the ATCC (CCL-213). Daudi cells were thawed and cultured in RPMI-1640 Medium (GIBCO #21870) with 10% FBS, 2 mM L-Glutamine, 100 units/ml penicillin, and 100 ug/ml streptomycin (GIBCO #15140-122). Daudi cells were incubated at 37° C. in a humidified atmosphere containing 5% CO2. RPMI growth medium was changed and cultures were split at a ratio of 1:10 every two to three days. Daudi cell viability was determined by Trypan blue exclusion. Rituximab (Cat #680563) was purchased from Biogen Idec. Mice that were not injected with tumor cells or with rituximab were used as additional controls. At 10 days post-engraftment, cohorts of mice were injected intraperitoneally (IP) with either with rituximab (25 μg/g) in 200 uL of PBS or with 200 uL of PBS only. Tumor engrafted mice were monitored three times per week and euthanized by CO2 asphyxiation followed by thoracic puncture, when they exhibited hind leg paralysis or showed >20% weight loss. Tumor burden and tumor invasiveness in mice were evaluated via flow cytometry, histology, and immunohistochemistry. Statistical differences in survival between the treated and control groups were analyzed by Kaplan-Meier plots provided using Prism statistical software. Statistical analysis was performed using the Log-Rank test and differences were considered significant at the P-value of <0.05.

Body Weight and Hind Limb Paralysis

Figure 2A:
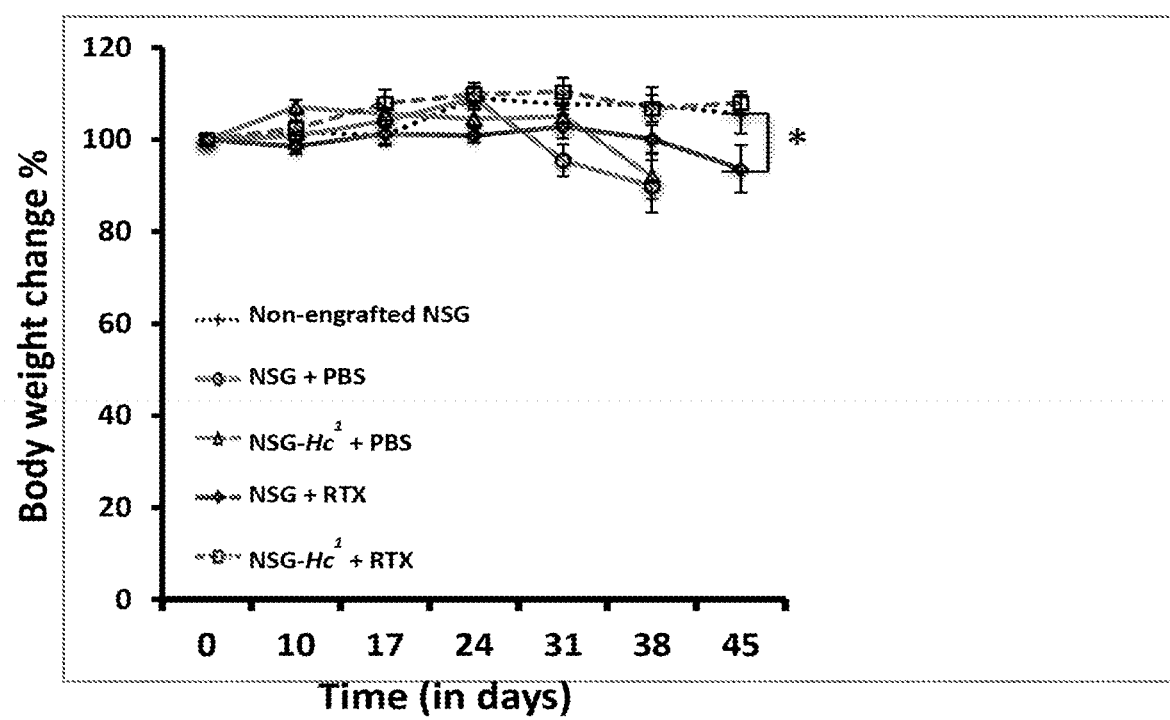
FIG. 2A shows a representative graph of the change in body weight over time in different cohorts of age and sex matched NSG and NSG-Hc$^1$ mice engrafted with 1×10$^5$ Daudi cells via intravenous injections, and at 10 days post engraftment injected with either 25 μg/g of rituximab or PBS. Non-engrafted NSG mice were used as negative controls. PBS, phosphate buffer saline; RTX, rituximab. Data are reported as percentage of the mean±SE. *P<0.05.

At 38 days post-injection of Daudi cells, a significant weight loss and hind limb paralysis was observed in the PBS treated mice when compared to rituximab treated mice, FIG. 2A. All mice in the PBS treated cohorts had either >20% weight loss or showed hind limb paralysis and were euthanized by 42 days post-engraftment. Rituximab treatment resulted in a significant complement-independent delayed loss of body weight and hind limb paralysis, when compared to PBS treated mice cohorts, (p<0.05), FIG. 2A. On the other hand, no loss of body weight was observed in rituximab treated NSG-Hc[1] mice throughout the study period, i.e. 52 days post-engraftment, suggesting that functional complement system in NSG-Hc[1] mice when treated with Rituximab mice significantly hindered weight loss and hind limb paralysis by mediating effective CDC activity against human tumor cells FIG. 2A.

Survival

Figure 2B:
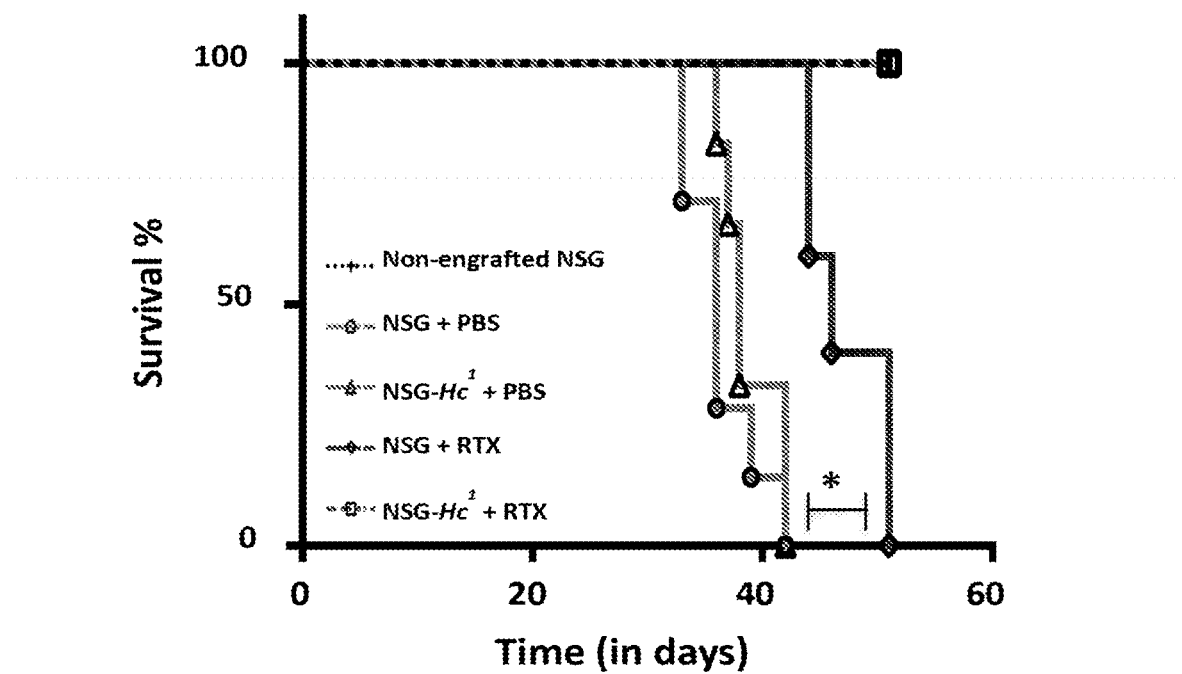
FIG. 2B shows a representative Kaplan-Meier survival plot demonstrating percent survival over time in different cohorts of age and sex matched NSG and NSG-Hc$^1$ mice engrafted with 1×10$^5$ Daudi cells via intravenous injections, and at 10 days post engraftment injected with either 25 μg/g of rituximab or PBS. Non-engrafted NSG mice were used as negative controls. PBS, phosphate buffer saline; RTX, rituximab. Data are reported as percentage of the mean±SE. *P<0.05.

At 38 days post-injection of Daudi cells, no significant difference in overall survival was observed between PBS treated NSG mice (median survival=36 days) and PBS treated NSG-Hc[1] mice (median survival=38 days), FIG. 2B. Rituximab treatment resulted in a significant complement-independent increase in the overall survival in NSG mice (median survival=46 days), when compared to PBS treated mice cohorts, (p<0.05), FIG. 2B. On the other hand, there was 100 percent survival observed in rituximab treated NSG-Hc[1] mice throughout the study period, i.e. 52 days post-engraftment, suggesting that functional complement system in NSG-Hc[1] mice when treated with rituximab mice significantly improved mouse survival by mediating effective CDC activity against human tumor cells, FIG. 2B.

Distant Metastasis

For flow cytometry analysis, peripheral blood was collected from mice by puncture of the retro-orbital venous plexus directly into flow tubes containing FACS buffer (PBS containing 2% FBS and 0.01% $NaN_3$). Mice were then euthanized by CO2 asphyxiation or cervical dislocation. Bone marrow was collected by flushing from femur. Spleen cells were collected following mechanical disaggregation. Single-cell suspensions prepared from blood, spleen and bone marrow were subjected to RBC lysis using ACK lysis buffer and washed twice before blocking in rabbit immunoglobulin commercially purchased form Sigma-Aldrich. Blocked RBC depleted cells were stained using fluorescently conjugated antibodies to anti-human CD45 antibody from BD Biosciences (clone HI30), anti-mouse CD45 antibody (clone A20) and anti-human CD20 antibody (clone 2H7) from BioLegend. All phenotyping analyses were carried out by flow cytometry using FACSCalibur (Becton Dickinson) and data were processed by FlowJo software.

Figure 3A:
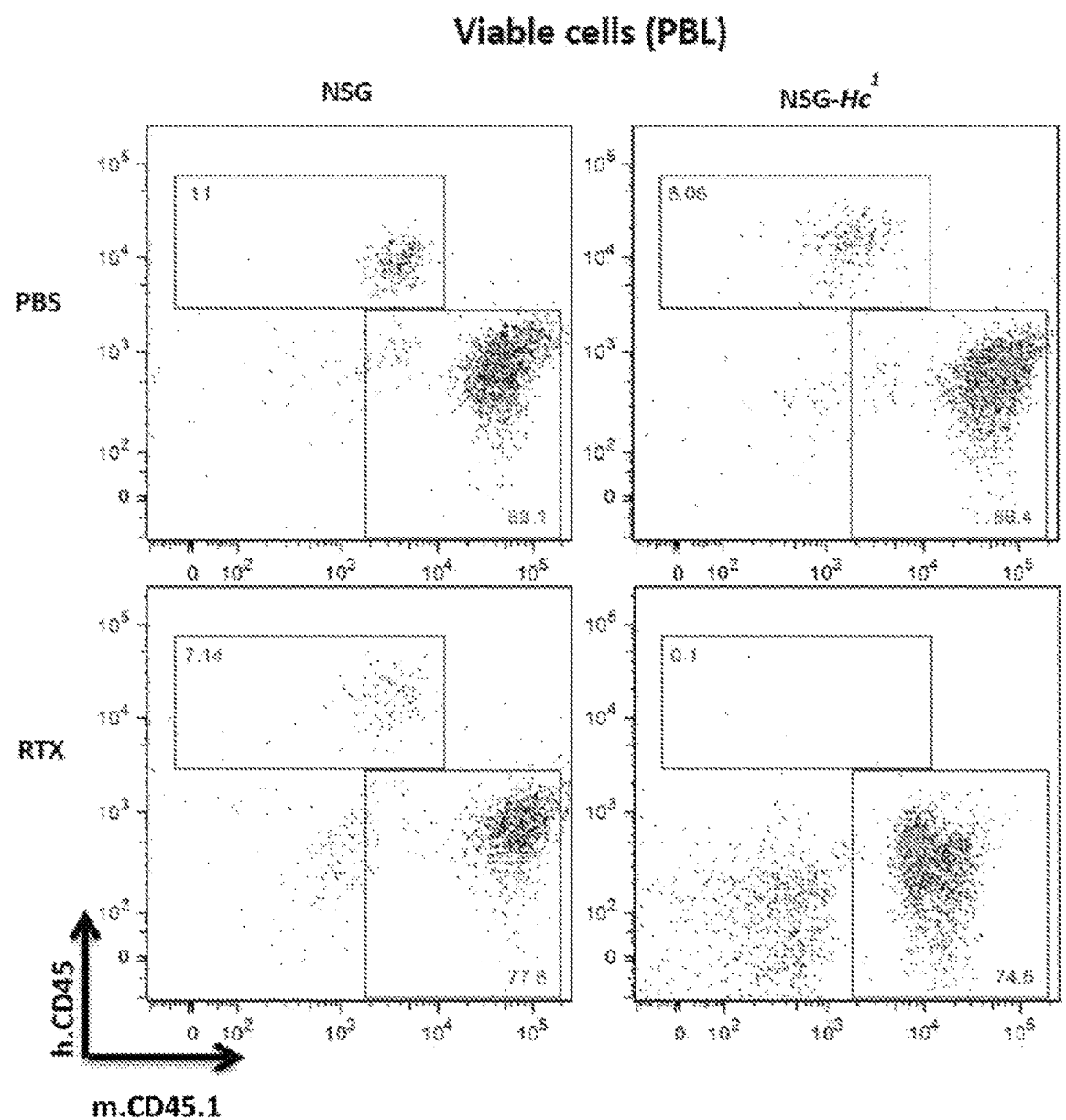
FIG. 3A shows representative flow cytometry analysis of peripheral blood lymphocytes in different cohorts of age and sex matched NSG and NSG-Hc$^1$ engrafted with 1×10$^5$ Daudi cells via intravenous injections, and at 10 days post engraftment injected with either 25 μg/g of rituximab or PBS. Non-engrafted NSG mice were used as negative controls. Measurements were taken 38 day post-engraftment. Data are reported as the mean±SD. PBS, phosphate buffer saline; RTX, rituximab; *P<0.05.
Figure 3A:
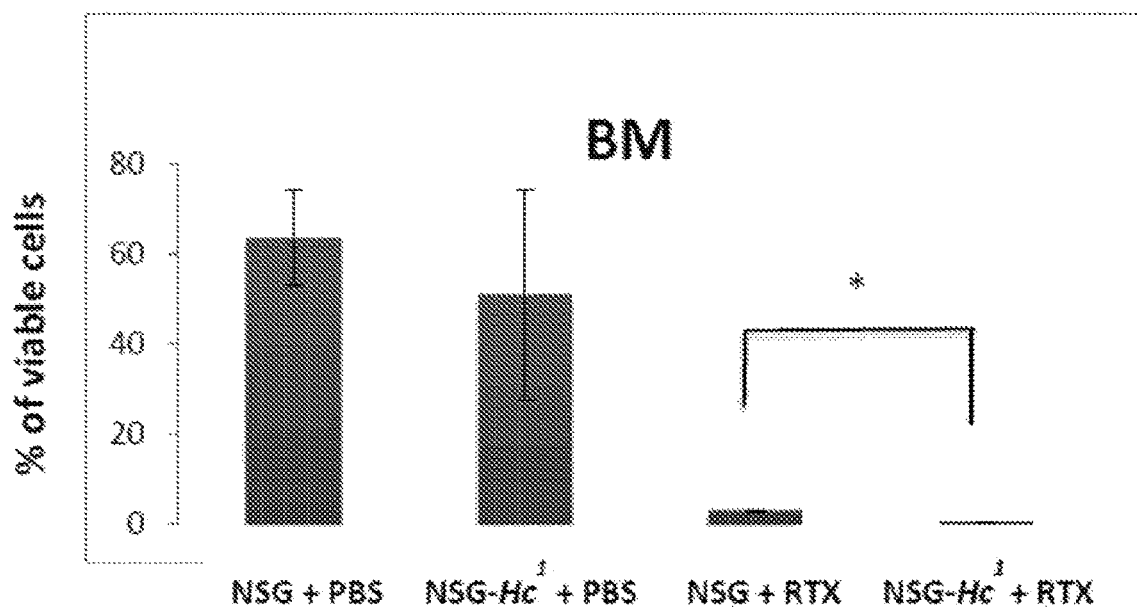
Figure 3B:
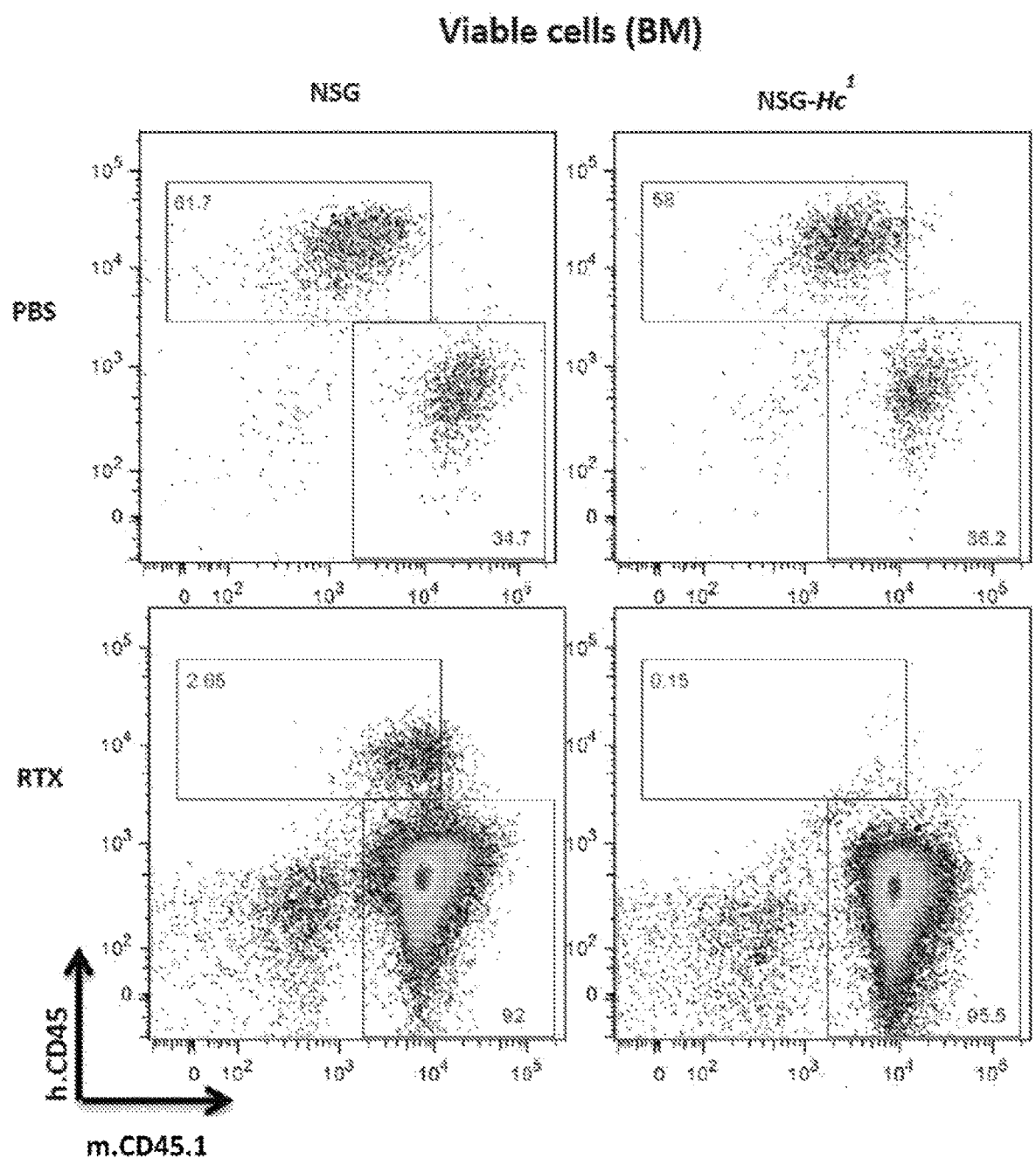
FIG. 3B shows representative flow cytometry analysis of bone marrow in different cohorts of age and sex matched NSG and NSG-Hc$^1$ engrafted with 1×10$^5$ Daudi cells via intravenous injections, and at 10 days post engraftment injected with either 25 μg/g of rituximab or PBS. Non-engrafted NSG mice were used as negative controls. Measurements were taken 38 day post-engraftment. Data are reported as the mean±SD. PBS, phosphate buffer saline; RTX, rituximab; *P<0.05.
Figure 3B:
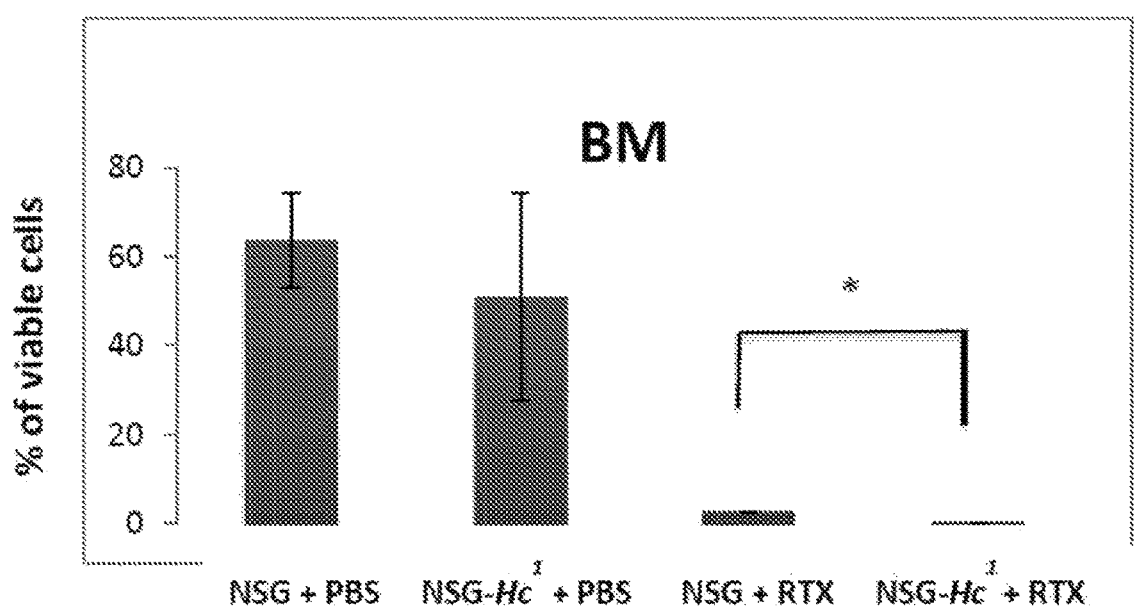

Flow cytometry analysis of circulating human CD45+ Daudi cells in peripheral blood and bone marrow at 38 days post-engraftment also confirmed the CDC mediated antitumor active in NSG-Hc[1] mice as we observed significantly lower numbers of human CD45+ Daudi cells in peripheral blood and bone marrow of the rituximab treated NSG-Hc[1] mice when compared to rituximab treated NSG mice, (p<0.05), FIG. 3A and FIG. 3B.

For histology analysis, mice were euthanized by CO2 asphyxiation followed by either cervical dislocation or thoracic puncture. Complete necropsy of the animals was performed and tissues were fixed in 10% neutral buffered formalin (NBF) solution, embedded in paraffin and sectioned at 3-5 µm. Slides were stained with either Mayer's hematoxylin and eosin (H&E) or anti-human CD45 antibody from Dako (clone 2B11+PD7/26). Qualitative detection of human CD45 antigen was done using DISCOVERY DAB Map Detection Kit (RUO) from Ventana and photographs were taken with a photomicroscope (Olympus BX41).

Figure 4A:
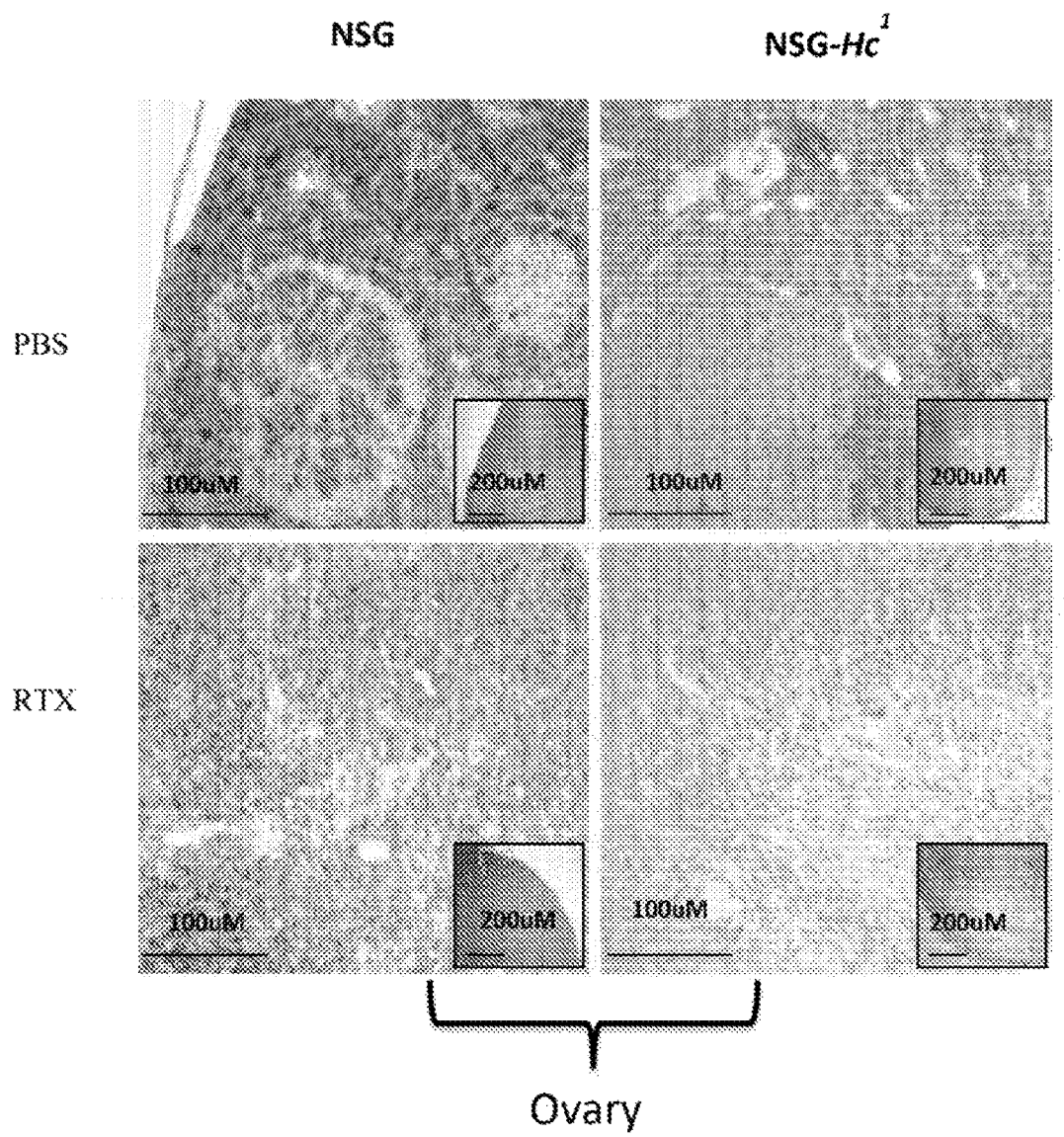
FIG. 4A shows representative images of the ovary displaying levels of Daudi cells engraftment in different cohorts of age and sex matched NSG and NSG-Hc$^1$ mice engrafted with 1×10$^5$ Daudi cells via intravenous injections, and at 10 days post engraftment injected with either 25 μg/g of rituximab or PBS. Measurements were taken 38 day post-engraftment. Original magnification ×10 (scale bar=200 μM) showing HE staining; high-magnification image ×20 scale bar=100 μm showing anti-human CD45 IHC. PBS, phosphate buffer saline; RTX, rituximab.
Figure 4B:
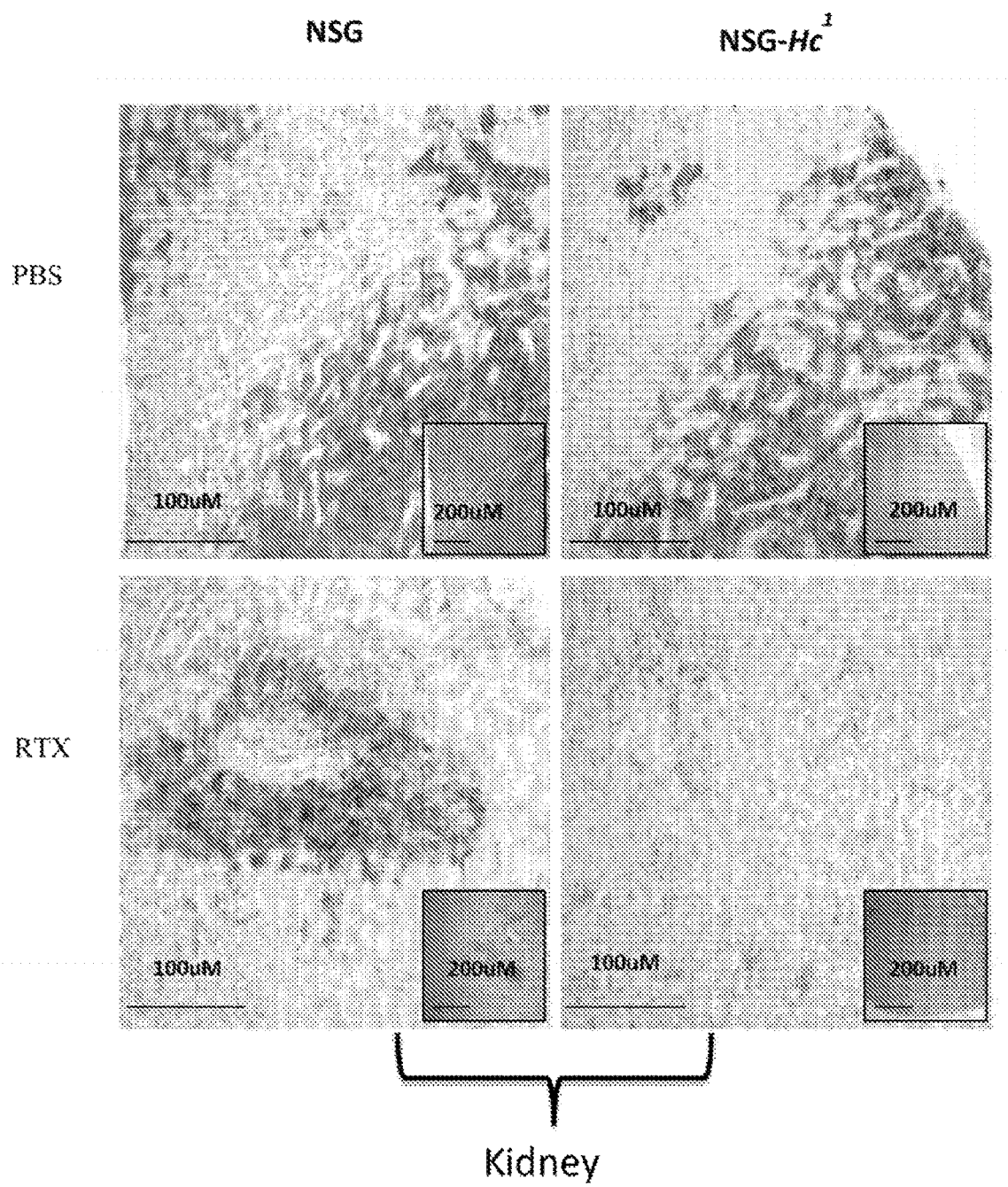
FIG. 4B shows representative images of the kidney displaying levels of Daudi cell engraftment in different cohorts of age and sex matched NSG and NSG-Hc$^1$ mice engrafted with 1×10$^5$ Daudi cells via intravenous injections, and at 10 days post engraftment injected with either 25 μg/g of rituximab or PBS. Measurements were taken 38 day post-engraftment. Original magnification ×10 (scale bar=200 μM) showing HE staining; high-magnification image ×20 scale bar=100 μm showing anti-human CD45 IHC. PBS, phosphate buffer saline; RTX, rituximab.

Moreover, as expected histological analysis of various organs, including ovary, kidney, liver, spleen, lungs, lymph nodes etc., of mice at 38 days post-engraftment demonstrated reduced numbers of Daudi cells in tissues from rituximab treated NSG-Hc[1] mice compared to other groups of mice, FIG. 4A and FIG. 4B.

SEQUENCES

*Mus musculus* C5 complement component structural protein amino acid sequence (SEQ ID NO:1):

MGLWGILCLLIFLDKTWGQEQTYVISAPKILRVGSSENVVIQVHGYTEAF

DATLSLKSYPDKKVTFSSGYVNLSPENKFQNAALLTLQPNQVPREESPVS

HVYLEVVSKHFSKSKKIPITYNNGILFIHTDKPVYTPDQSVKIRVYSLGD

DLKPAKRETVLTFIDPEGSEVDIVEENDYTGIISFPDFKIPSNPKYGVWT

IKANYKKDFTTTGTAYFEIKEYVLPRFSVSIELERTFIGYKNFKNFEITV

KARYFYNKVVPDAEVYAFFGLREDIKDEEKQMMHKATQAAKLVDGVAQIS

FDSETAVKELSYNSLEDLNNKYLYIAVTVTESSGGFSEEAEIPGVKYVLS

PYTLNLVATPLFVKPGIPFSIKAQVKDSLEQAVGGVPVTLMAQTVDVNQE

TSDLETKRSITHDTDGVAVFVLNLPSNVTVLKFEIRTDDPELPEENQASK

EYEAVAYSSLSQSYIYIAWTENYKPMLVGEYLNIMVTPKSPYIDKITHYN

YLILSKGKIVQYGTREKLFSSTYQNINIPVTQNMVPSARLLVYYIVTGEQ

TAELVADAVWINIEEKCGNQLQVHLSPDEYVYSPGQTVSLDMVTEADSWV

ALSAVDRAVYKVQGNAKRAMQRVFQALDEKSDLGCGAGGGHDNADVFHLA

GLTFLTNANADDSHYRDDSCKEILRSKRNLHLLRQKIEEQAAKYKHSVPK

KCCYDGARVNFYETCEERVARVTIGPLCIRAFNECCTIANKIRKESPHKP

VQLGRIHIKTLLPVMKADIRSYFPESWLWEIHRVPKRKQLQVTLPDSLTT

WEIQGIGISDNGICVADTLKAKVFKEVFLEMNIPYSVVRGEQIQLKGTVY

NYMTSGTKFCVKMSAVEGICTSGSSAASLHTSRPSRCVFQRIEGSSSHLV

TFTLLPLEIGLHSINFSLETSFGKDILVKTLRVVPEGVKRESYAGVILDP

KGIRGIVNRRKEFPYRIPLDLVPKTKVERILSVKGLLVGEFLSTVLSKEG

INILTHLPKGSAEAELMSIAPVFYVFHYLEAGNHWNIFYPDTLSKRQSLE

KKIKQGVVSVMSYRNADYSYSMWKGASASTWLTAFALRVLGQVAKYVKQD

ENSICNSLLWLVEKCQLENGSFKENSQYLPIKLQGTLPAEAQEKTLYLTA

FSVIGIRKAVDICPTMKIHTALDKADSFLLENTLPSKSTFTLAIVAYALS

LGDRTHPRFRLIVSALRKEAFVKGDPPIYRYWRDTLKRPDSSVPSSGTAG

MVETTAYALLASLKLKDMNYANPIIKWLSEEQRYGGGFYSTQDTINAIEG

LTEYSLLLKQIHLDMDINVAYKHEGDFHKYKVTEKHFLGRPVEVSLNDDL

VVSTGYSSGLATVYVKTVVHKISVSEEFCSFYLKIDTQDIEASSHFRLSD

SGFKRIIACASYKPSKEESTSGSSHAVMDISLPTGIGANEEDLRALVEGV

DQLLTDYQIKDGHVILQLNSIPSRDFLCVRFRIFELFQVGFLNPATFTVY

EYHRPDKQCTMIYSISDTRLQKVCEGAACTCVEADCAQLQAEVDLAISAD

SRKEKACKPETAYAYKVRITSATEENVFVKYTATLLVTYKTGEAADENSE

VTFIKKMSCTNANLVKGKQYLIMGKEVLQIKHNFSFKYIYPLDSSTWIEY

WPTDTTCPSCQAFVENLNNFAEDLFLNSCE

53

Example 3

Complement Assay
Reagents
Sheep RBCs from Grainger, cat #10H72, 20 mLs
Rabbit anti sheep RBC from Grainger, Cat #10K945, 2 mL, Reconstitute with 2 mLs H2O, aliquot and freeze at −80.
Guinea Pig Complement from Grainger, Cat #10H654, 5 mLs. Reconstitute with 5 mLs distilled $H_2O$, aliquot and freeze at −80.
HBSS from Gibco, #14025
Overview—each well will have a total of 200 µLs: 175 µLs of lysis control or diluted serum, and 25 µLs of antibody coated sheep RBCs.
Complement assay protocol:
Wash Sheep RBCs (2.5 mL/plate, 25 µLs/well) in HBSS.
Prepare EA (antibody sensitized sheep red blood cells)
Add $1*10^9$ RBC (~1 mL) to eppendorf tube and mix with anti-SRBC antibody @ 1:10 dilution (scale up for the number of wells; 25 µL/well)
Incubate at 37 C for 30 min, then spin down 5 min @ 350×g and resuspend in the original volume of HBSS
Prepare samples
Add 120 µL serum to 405 µL HBSS. After adding the SRBC, this will be a 1:5 dilution. This is enough serum for triplicate wells.
Lysis controls: for 0% lysis use HBSS; for 100% lysis, use ACK buffer
Prepare plate
1. Will need three wells for each control, serum, and blank.
2. Controls: HBSS for 0%, ACK for 100%, Guinea Pig Complement diluted 1:10, HBSS alone for a plate blank.
3. Add 175 µL of lysis controls or diluted serum to their respective wells of a V-bottom plate
4. Add 25 µL EA suspension to every well except for the blanks.
5. Cover with a plate sealer for lid and incubate for 1 hr at 37 C with gentle tapping/shaking every 10 min or so
6. Centrifuge the plate for 5 min @ 1250×g to pellet cells.
7. Transfer 100 µL supernatant from each well to its corresponding well on a 96-well ELISA plate and read @ OD540.
Calculate results (expressed as % lysis)

Find relative absorbance (RA) as RA=(abs of sample)−(abs of 0% lysis well)

Find % lysis as Percent RBC lysis=((RA of sample well)/(RA of 100% lysis well))*100

Serums from LDS 6564 diluted 1:5 in HBSS (120 µLs serum+405 µLs HBSS) and run in triplicate.

| 1 | 2 | 3 | 4 | 5 | 6 | 7 | 8 | 9 | 10 | 11 | 12 |
|---|---|---|---|---|---|---|---|---|----|----|----|
| HBSS (0%) | | | 10 NSG | | | | | | | | |
| H2O (100%) | | | 12 NSG | | | | | | | | |
| ACK (100%) | | | 14 NSG | | | | | | | | |
| GPC 1:5 | | | HBSS (blank) | | | | | | | | |
| HBSS (blank) | | | 31 NSG-Hc | | | | | | | | |
| 1 Balb | | | 32 NSG-Hc | | | | | | | | |
| 2 Balb | | | 33 NSG-Hc | | | | | | | | |
| 3 Balb | | | HBSS (blank) | | | | | | | | |

54

Enough space to run 24 samples in triplicate, or 80 samples in duplicate
Additional information:
Strain Name:
NOD.CBALs-Hc[1]/LtJ
Common Name: NOD.Hc[1]
Appearance: albino, pink eyed
Related Genotype: A/A Tyrc/Tyrc
Description: This NOD/Lt congenic strain is carrying Chr 2 alleles derived from CBA/Ls including Hc[1]. Diabetes onset and incidence is the same as NOD/Lt.
Development: C5 hemolytic complement located on Chr. 2 was transferred from CBA/Ls to NOD/Lt for 10 generations replacing the defective Hc[o] allele expressed in NOD/Lt. T1DR has homozygous NOD.CBALs-Hc[1]/Lt at generation N10F11.
Items
Item 1.
A genetically modified immunodeficient non-human animal, wherein the genome of the non-human animal comprises a repaired C5 complement component structural gene such that the genetically modified immunodeficient non-human animal expresses the C5 complement component structural gene and is characterized by an intact complement system.
Item 2. The genetically modified immunodeficient non-human animal of item 1 wherein the animal has severe combined immunodeficiency.
Item 3. The genetically modified immunodeficient non-human animal of item 1 or 2, wherein the animal has an IL2 receptor gamma chain deficiency.
Item 4. The genetically modified immunodeficient non-human animal of any of items 1, 2 or 3, wherein the animal has a recombination activating gene 1 deficiency.
Item 5. The genetically modified immunodeficient non-human animal of any of items 1 to 4, wherein the animal has a recombination activating gene 2 deficiency.
Item 6. The genetically modified immunodeficient non-human animal of any of items 1 to 5, wherein the animal is a mouse.
Item 7. The genetically modified immunodeficient non-human animal of item 6, wherein the mouse is a NOD mouse comprising a scid mutation.
Item 8. The genetically modified immunodeficient non-human animal of item 7, wherein the NOD mouse is homozygous for the scid mutation.
Item 9. The genetically modified immunodeficient non-human animal of any of items 6, 7 or 8, wherein the mouse is a NOD mouse comprising a Rag1 mutation.
Item 10. The genetically modified immunodeficient non-human animal of any of items 6 to 9, wherein the NOD mouse is homozygous for the Rag1 mutation.
Item 11. The genetically modified immunodeficient non-human animal of any of items 6 to 10, wherein the mouse is a NOD mouse comprising a Rag1$^{tm1Mom}$ mutation.
Item 12. The genetically modified immunodeficient non-human animal of any of items 6 to 11, wherein NOD mouse is homozygous for the Rag1$^{tm1Mom}$ mutation.
Item 13. The genetically modified immunodeficient non-human animal of item 1, wherein the genetically modified immunodeficient non-human animal is an NSG-Hc[1] mouse comprising a repaired C5 complement component structural gene such that the genetically modified NSG mouse expresses the C5 complement component structural gene and is characterized by an intact complement system.
Item 14. The genetically modified immunodeficient non-human animal of item 1, wherein the genetically modified immunodeficient non-human animal is an NRG-Hc[1] mouse comprising a repaired C5 complement component structural gene such that the genetically modified NRG mouse expresses the C5 complement component structural gene and is characterized by an intact complement system.

Item 15. The genetically modified immunodeficient non-human animal of item 1, wherein the genetically modified immunodeficient non-human animal is a NOG-Hc$^1$ mouse comprising a repaired C5 complement component structural gene such that the genetically modified NOG mouse expresses the C5 complement component structural gene and is characterized by an intact complement system.

Item 16. The genetically modified immunodeficient non-human animal of any of items 1 to 15, further comprising xenograft tumor cells.

Item 17. The genetically modified immunodeficient non-human animal of any of items 1 to 16, further comprising human xenograft tumor cells.

Item 18. The genetically modified immunodeficient non-human animal of any of items 1 to 17, further comprising xenograft tumor cells of a cell line.

Item 19. A method for producing a non-human animal model system for assessment of an anti-cancer therapeutic or putative anti-cancer therapeutic, comprising: providing a non-human genetically modified immunodeficient animal comprising a repaired C5 complement component structural gene such that the non-human genetically modified immunodeficient animal expresses the C5 complement component structural gene and is characterized by an intact complement system; and administering xenograft tumor cells to the non-human genetically modified immunodeficient animal.

Item 20. The method of item 19, wherein the non-human genetically modified immunodeficient animal has severe combined immunodeficiency.

Item 21. The method of item 19 or 20, wherein the non-human genetically modified immunodeficient animal has an IL2 receptor gamma chain deficiency.

Item 22. The method of any of items 19, 20 or 21, wherein the non-human genetically modified immunodeficient animal has a recombination activating gene 1 deficiency.

Item 23. The method of any of items 19 to 22, wherein the non-human genetically modified immunodeficient animal has a recombination activating gene 2 deficiency.

Item 24. The method of any of items 19 to 23, wherein the non-human genetically modified immunodeficient animal is a mouse.

Item 25. The method of item 24, wherein the mouse is a NOD mouse comprising the scid mutation and having a severe combined immunodeficiency.

Item 26. The method of item 25, wherein the NOD mouse is homozygous for the scid mutation and has a severe combined immunodeficiency.

Item 27. The method of any of items 24, 25 or 26, wherein the mouse is a NOD mouse comprising a Rag1 mutation and having a RAG 1 deficiency.

Item 28. The method of any of items 24 to 27, wherein the NOD mouse is homozygous for the Rag1 mutation and has a RAG 1 deficiency.

Item 29. The method of any of items 24 to 28, wherein the mouse is a NOD mouse comprising a Rag1$^{tm1Mom}$ mutation and having a RAG 1 deficiency.

Item 30. The method of any of items 24 to 29, wherein the NOD mouse is homozygous for the Rag1$^{tm1Mom}$ mutation and has a RAG 1 deficiency.

Item 30. The method of any of items 24 to 26, wherein the mouse is a NSG-Hc$^1$ mouse.

Item 31. The method of any of items 24 and 27 to 30, wherein the mouse is a NRG-Hc$^1$ mouse.

Item 32. The method of item 24, wherein the mouse is a NOG-Hc$^1$ mouse.

Item 33. The method of any of items 19 to 32, wherein the xenograft tumor cells are human xenograft tumor cells Item 34. The method of any of items 19 to 33, wherein the xenograft tumor cells are xenograft tumor cells of a cell line.

Item 35. A method for assessing the effect of an anti-cancer therapeutic or putative anti-cancer therapeutic, comprising: providing a non-human genetically modified immunodeficient animal comprising a repaired C5 complement component structural gene such that the non-human genetically modified immunodeficient animal expresses the C5 complement component structural gene and is characterized by an intact complement system; administering xenograft tumor cells to the non-human genetically modified immunodeficient animal; administering an anti-cancer therapeutic or putative anti-cancer therapeutic to the animal; and assaying a response of the xenograft tumor cells to the anti-cancer therapeutic.

Item 36. The method of item 35 wherein the anti-cancer therapeutic or putative anti-cancer therapeutic is an antibody.

Item 37. The method of item 35 or 36, wherein the non-human genetically modified immunodeficient animal has severe combined immunodeficiency.

Item 38. The method of item 35, 36 or 37, wherein the non-human genetically modified immunodeficient animal has an IL2 receptor gamma chain deficiency.

Item 39. The method of any of items 35 to 38, wherein the non-human genetically modified immunodeficient animal has a recombination activating gene 1 deficiency.

Item 40. The method of any of items 35 to 39, wherein the non-human genetically modified immunodeficient animal has a recombination activating gene 2 deficiency.

Item 41. The method of any of items 35 to 40, wherein the non-human genetically modified immunodeficient animal is a mouse.

Item 42. The method of item 41, wherein the mouse is a NOD mouse comprising a scid mutation and having a severe combined immunodeficiency.

Item 43. The method of item 41 or 42, wherein the NOD mouse is homozygous for the scid mutation and has a severe combined immunodeficiency.

Item 44. The method of any of items 41, 42 or 43, wherein the mouse is a NOD mouse comprising a Rag1$^{tm1Mom}$ mutation and having a RAG 1 deficiency.

Item 45. The method of any of items 41 to 44, wherein NOD mouse is homozygous for the Rag1$^{tm1Mom}$ mutation and has a RAG 1 deficiency.

Item 46. The method of any of items 41, 42 or 43, wherein the mouse is an NSG-Hc$^1$ mouse.

Item 47. The method of any of items 41, 44 or 45, wherein the mouse is a NRG-Hc$^1$ mouse.

Item 48. The method of any of items 35 to 47, wherein the xenograft tumor cells are human xenograft tumor cells.

Item 49. The method of any of items 35 to 48, wherein the xenograft tumor cells are xenograft tumor cells of a cell line.

Item 50. A genetically modified NSG mouse, wherein the genome of the non-human animal comprises a repaired C5 complement component structural gene such that the genetically modified NSG mouse expresses the C5 complement component structural gene and is characterized by an intact complement system substantially as described herein.

Item 51. A genetically modified NRG mouse, wherein the genome of the non-human animal comprises a repaired C5 complement component structural gene such that the genetically modified NRG mouse expresses the C5 complement component structural gene and is characterized by an intact complement system substantially as described herein.

Item 52. A genetically modified NOG mouse, wherein the genome of the non-human animal comprises a repaired C5 complement component structural gene such that the genetically modified NOG mouse expresses the C5 complement component structural gene and is characterized by an intact complement system substantially as described herein.

Item 53. A method for producing a non-human animal model system for assessment of an anti-cancer therapeutic substantially as described herein.

Item 54. A method for assessing the effect of an anti-cancer therapeutic in a non-human animal model system substantially as described herein.

Any patents or publications mentioned in this specification are incorporated herein by reference to the same extent as if each individual publication is specifically and individually indicated to be incorporated by reference.

The non-human animals, compositions and methods of the present invention described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

---

The invention claimed is:

1. An immunodeficient mouse, wherein the genome of the mouse comprises a non-obese diabetic (NOD) background and an endogenous wild-type *Mus musculus* Hc$^1$ Allele encoding a functional C5 complement component structural protein, and wherein the functional C5 complement component structural protein is expressed in the mouse.

2. The immunodeficient mouse of claim 1 wherein the mouse has the severe combined immunodeficiency mutation Prkdc$^{scid}$ and/or an IL2 receptor gamma (IL2Rg) mutation.

3. The immunodeficient mouse of claim 1, wherein the genotype of the mouse is NSG-Hc$^1$.

4. The immunodeficient mouse of claim 1, wherein the genotype of the mouse is NRG-Hc$^1$.

5. The immunodeficient mouse of claim 1, wherein the genotype of the mouse is NOG-Hc$^1$.

6. The immunodeficient mouse of claim 1, further comprising xenograft tumor cells.

7. The immunodeficient mouse of claim 1, further comprising human xenograft tumor cells.

8. The immunodeficient mouse of claim 1, further comprising xenograft tumor cells of a cell line.

9. The immunodeficient mouse of claim 8, wherein the cell line is a lymphoma cell line.

10. A method for producing a mouse model system for assessment of an anti-cancer therapeutic or putative anti-cancer therapeutic, comprising:
administering xenograft tumor cells to the immunodeficient mouse of claim 1.

11. A method for assessing the effect of an anti-cancer therapeutic antibody or putative anti-cancer therapeutic antibody, comprising:
administering xenograft tumor cells to the immunodeficient mouse of claim 1;
administering an anti-cancer therapeutic antibody or putative anti-cancer therapeutic antibody to the immunodeficient mouse; and
assaying a response of the xenograft tumor cells to the anti-cancer therapeutic antibody.

12. The immunodeficient mouse of claim 1, wherein complement dependent cytotoxicity in the mouse is increased by 70%-90% relative to an genetically modified immunodeficient mouse comprising a defective Hc$^0$ allele.

* * * * *

UNITED STATES PATENT AND TRADEMARK OFFICE
CERTIFICATE OF CORRECTION

| | | |
|---|---|---|
| PATENT NO. | : 11,785,923 B2 | Page 1 of 1 |
| APPLICATION NO. | : 16/886289 | |
| DATED | : October 17, 2023 | |
| INVENTOR(S) | : Leonard D. Shultz et al. | |

It is certified that error appears in the above-identified patent and that said Letters Patent is hereby corrected as shown below:

In the Claims

In Claim 12, Column 68, Line 48, the text "genetically modified" should be removed Signed and Sealed this
Fourteenth Day of November, 2023

Katherine Kelly Vidal
*Director of the United States Patent and Trademark Office*

SEQUENCE LISTING

<160> NUMBER OF SEQ ID NOS: 7

<210> SEQ ID NO 1
<211> LENGTH: 1680
<212> TYPE: PRT
<213> ORGANISM: Mus musculus

<400> SEQUENCE: 1

```
Met Gly Leu Trp Gly Ile Leu Cys Leu Leu Ile Phe Leu Asp Lys Thr
1               5                   10                  15

Trp Gly Gln Glu Gln Thr Tyr Val Ile Ser Ala Pro Lys Ile Leu Arg
            20                  25                  30

Val Gly Ser Ser Glu Asn Val Val Ile Gln Val His Gly Tyr Thr Glu
        35                  40                  45

Ala Phe Asp Ala Thr Leu Ser Leu Lys Ser Tyr Pro Asp Lys Lys Val
    50                  55                  60

Thr Phe Ser Ser Gly Tyr Val Asn Leu Ser Pro Glu Asn Lys Phe Gln
65                  70                  75                  80

Asn Ala Ala Leu Leu Thr Leu Gln Pro Asn Gln Val Pro Arg Glu Glu
                85                  90                  95

Ser Pro Val Ser His Val Tyr Leu Glu Val Val Ser Lys His Phe Ser
            100                 105                 110

Lys Ser Lys Lys Ile Pro Ile Thr Tyr Asn Asn Gly Ile Leu Phe Ile
        115                 120                 125

His Thr Asp Lys Pro Val Tyr Thr Pro Asp Gln Ser Val Lys Ile Arg
    130                 135                 140

Val Tyr Ser Leu Gly Asp Asp Leu Lys Pro Ala Lys Arg Glu Thr Val
145                 150                 155                 160

Leu Thr Phe Ile Asp Pro Glu Gly Ser Glu Val Asp Ile Val Glu Glu
                165                 170                 175

Asn Asp Tyr Thr Gly Ile Ile Ser Phe Pro Asp Phe Lys Ile Pro Ser
            180                 185                 190

Asn Pro Lys Tyr Gly Val Trp Thr Ile Lys Ala Asn Tyr Lys Lys Asp
        195                 200                 205

Phe Thr Thr Thr Gly Thr Ala Tyr Phe Glu Ile Lys Glu Tyr Val Leu
    210                 215                 220

Pro Arg Phe Ser Val Ser Ile Glu Leu Glu Arg Thr Phe Ile Gly Tyr
225                 230                 235                 240

Lys Asn Phe Lys Asn Phe Glu Ile Thr Val Lys Ala Arg Tyr Phe Tyr
                245                 250                 255

Asn Lys Val Val Pro Asp Ala Glu Val Tyr Ala Phe Phe Gly Leu Arg
            260                 265                 270
```

```
Glu Asp Ile Lys Asp Glu Glu Lys Gln Met Met His Lys Ala Thr Gln
            275                 280                 285

Ala Ala Lys Leu Val Asp Gly Val Ala Gln Ile Ser Phe Asp Ser Glu
        290                 295                 300

Thr Ala Val Lys Glu Leu Ser Tyr Asn Ser Leu Glu Asp Leu Asn Asn
305                 310                 315                 320

Lys Tyr Leu Tyr Ile Ala Val Thr Val Thr Glu Ser Ser Gly Gly Phe
                325                 330                 335

Ser Glu Glu Ala Glu Ile Pro Gly Val Lys Tyr Val Leu Ser Pro Tyr
            340                 345                 350

Thr Leu Asn Leu Val Ala Thr Pro Leu Phe Val Lys Pro Gly Ile Pro
        355                 360                 365

Phe Ser Ile Lys Ala Gln Val Lys Asp Ser Leu Glu Gln Ala Val Gly
370                 375                 380

Gly Val Pro Val Thr Leu Met Ala Gln Thr Val Asp Val Asn Gln Glu
385                 390                 395                 400

Thr Ser Asp Leu Glu Thr Lys Arg Ser Ile Thr His Asp Thr Asp Gly
            405                 410                 415

Val Ala Val Phe Val Leu Asn Leu Pro Ser Asn Val Thr Val Leu Lys
        420                 425                 430

Phe Glu Ile Arg Thr Asp Asp Pro Glu Leu Pro Glu Glu Asn Gln Ala
    435                 440                 445

Ser Lys Glu Tyr Glu Ala Val Ala Tyr Ser Ser Leu Ser Gln Ser Tyr
    450                 455                 460

Ile Tyr Ile Ala Trp Thr Glu Asn Tyr Lys Pro Met Leu Val Gly Glu
465                 470                 475                 480

Tyr Leu Asn Ile Met Val Thr Pro Lys Ser Pro Tyr Ile Asp Lys Ile
            485                 490                 495

Thr His Tyr Asn Tyr Leu Ile Leu Ser Lys Gly Lys Ile Val Gln Tyr
        500                 505                 510

Gly Thr Arg Glu Lys Leu Phe Ser Ser Thr Tyr Gln Asn Ile Asn Ile
    515                 520                 525

Pro Val Thr Gln Asn Met Val Pro Ser Ala Arg Leu Leu Val Tyr Tyr
    530                 535                 540

Ile Val Thr Gly Glu Gln Thr Ala Glu Leu Val Ala Asp Ala Val Trp
545                 550                 555                 560

Ile Asn Ile Glu Glu Lys Cys Gly Asn Gln Leu Gln Val His Leu Ser
            565                 570                 575

Pro Asp Glu Tyr Val Tyr Ser Pro Gly Gln Thr Val Ser Leu Asp Met
        580                 585                 590

Val Thr Glu Ala Asp Ser Trp Val Ala Leu Ser Ala Val Asp Arg Ala
    595                 600                 605

Val Tyr Lys Val Gln Gly Asn Ala Lys Arg Ala Met Gln Arg Val Phe
    610                 615                 620

Gln Ala Leu Asp Glu Lys Ser Asp Leu Gly Cys Gly Ala Gly Gly Gly
625                 630                 635                 640

His Asp Asn Ala Asp Val Phe His Leu Ala Gly Leu Thr Phe Leu Thr
            645                 650                 655

Asn Ala Asn Ala Asp Asp Ser His Tyr Arg Asp Asp Ser Cys Lys Glu
        660                 665                 670

Ile Leu Arg Ser Lys Arg Asn Leu His Leu Leu Arg Gln Lys Ile Glu
    675                 680                 685

Glu Gln Ala Ala Lys Tyr Lys His Ser Val Pro Lys Lys Cys Cys Tyr
```

-continued

```
            690                 695                 700
Asp Gly Ala Arg Val Asn Phe Tyr Glu Thr Cys Glu Arg Val Ala
705                     710                 715                 720
Arg Val Thr Ile Gly Pro Leu Cys Ile Arg Ala Phe Asn Glu Cys Cys
                    725                 730                 735
Thr Ile Ala Asn Lys Ile Arg Lys Glu Ser Pro His Lys Pro Val Gln
                740                 745                 750
Leu Gly Arg Ile His Ile Lys Thr Leu Leu Pro Val Met Lys Ala Asp
            755                 760                 765
Ile Arg Ser Tyr Phe Pro Glu Ser Trp Leu Trp Glu Ile His Arg Val
        770                 775                 780
Pro Lys Arg Lys Gln Leu Gln Val Thr Leu Pro Asp Ser Leu Thr Thr
785                 790                 795                 800
Trp Glu Ile Gln Gly Ile Gly Ile Ser Asp Asn Gly Ile Cys Val Ala
                    805                 810                 815
Asp Thr Leu Lys Ala Lys Val Phe Lys Glu Val Phe Leu Glu Met Asn
                820                 825                 830
Ile Pro Tyr Ser Val Val Arg Gly Glu Gln Ile Gln Leu Lys Gly Thr
            835                 840                 845
Val Tyr Asn Tyr Met Thr Ser Gly Thr Lys Phe Cys Val Lys Met Ser
850                 855                 860
Ala Val Glu Gly Ile Cys Thr Ser Gly Ser Ser Ala Ala Ser Leu His
865                 870                 875                 880
Thr Ser Arg Pro Ser Arg Cys Val Phe Gln Arg Ile Glu Gly Ser Ser
                    885                 890                 895
Ser His Leu Val Thr Phe Thr Leu Leu Pro Leu Glu Ile Gly Leu His
                900                 905                 910
Ser Ile Asn Phe Ser Leu Glu Thr Ser Phe Gly Lys Asp Ile Leu Val
            915                 920                 925
Lys Thr Leu Arg Val Val Pro Glu Gly Val Lys Arg Glu Ser Tyr Ala
930                 935                 940
Gly Val Ile Leu Asp Pro Lys Gly Ile Arg Gly Ile Val Asn Arg Arg
945                 950                 955                 960
Lys Glu Phe Pro Tyr Arg Ile Pro Leu Asp Leu Val Pro Lys Thr Lys
                    965                 970                 975
Val Glu Arg Ile Leu Ser Val Lys Gly Leu Leu Val Gly Glu Phe Leu
                980                 985                 990
Ser Thr Val Leu Ser Lys Glu Gly Ile Asn Ile Leu Thr His Leu Pro
            995                 1000                1005
Lys Gly Ser Ala Glu Ala Glu Leu Met Ser Ile Ala Pro Val Phe
        1010                1015                1020
Tyr Val Phe His Tyr Leu Glu Ala Gly Asn His Trp Asn Ile Phe
        1025                1030                1035
Tyr Pro Asp Thr Leu Ser Lys Arg Gln Ser Leu Glu Lys Lys Ile
        1040                1045                1050
Lys Gln Gly Val Val Ser Val Met Ser Tyr Arg Asn Ala Asp Tyr
        1055                1060                1065
Ser Tyr Ser Met Trp Lys Gly Ala Ser Ala Ser Thr Trp Leu Thr
        1070                1075                1080
Ala Phe Ala Leu Arg Val Leu Gly Gln Val Ala Lys Tyr Val Lys
        1085                1090                1095
Gln Asp Glu Asn Ser Ile Cys Asn Ser Leu Leu Trp Leu Val Glu
        1100                1105                1110
```

-continued

```
Lys Cys Gln Leu Glu Asn Gly Ser Phe Lys Glu Asn Ser Gln Tyr
1115                1120                1125

Leu Pro Ile Lys Leu Gln Gly Thr Leu Pro Ala Glu Ala Gln Glu
1130                1135                1140

Lys Thr Leu Tyr Leu Thr Ala Phe Ser Val Ile Gly Ile Arg Lys
1145                1150                1155

Ala Val Asp Ile Cys Pro Thr Met Lys Ile His Thr Ala Leu Asp
1160                1165                1170

Lys Ala Asp Ser Phe Leu Leu Glu Asn Thr Leu Pro Ser Lys Ser
1175                1180                1185

Thr Phe Thr Leu Ala Ile Val Ala Tyr Ala Leu Ser Leu Gly Asp
1190                1195                1200

Arg Thr His Pro Arg Phe Arg Leu Ile Val Ser Ala Leu Arg Lys
1205                1210                1215

Glu Ala Phe Val Lys Gly Asp Pro Pro Ile Tyr Arg Tyr Trp Arg
1220                1225                1230

Asp Thr Leu Lys Arg Pro Asp Ser Ser Val Pro Ser Ser Gly Thr
1235                1240                1245

Ala Gly Met Val Glu Thr Thr Ala Tyr Ala Leu Leu Ala Ser Leu
1250                1255                1260

Lys Leu Lys Asp Met Asn Tyr Ala Asn Pro Ile Ile Lys Trp Leu
1265                1270                1275

Ser Glu Glu Gln Arg Tyr Gly Gly Phe Tyr Ser Thr Gln Asp
1280                1285                1290

Thr Ile Asn Ala Ile Glu Gly Leu Thr Glu Tyr Ser Leu Leu Leu
1295                1300                1305

Lys Gln Ile His Leu Asp Met Asp Ile Asn Val Ala Tyr Lys His
1310                1315                1320

Glu Gly Asp Phe His Lys Tyr Lys Val Thr Glu Lys His Phe Leu
1325                1330                1335

Gly Arg Pro Val Glu Val Ser Leu Asn Asp Asp Leu Val Val Ser
1340                1345                1350

Thr Gly Tyr Ser Ser Gly Leu Ala Thr Val Tyr Val Lys Thr Val
1355                1360                1365

Val His Lys Ile Ser Val Ser Glu Glu Phe Cys Ser Phe Tyr Leu
1370                1375                1380

Lys Ile Asp Thr Gln Asp Ile Glu Ala Ser Ser His Phe Arg Leu
1385                1390                1395

Ser Asp Ser Gly Phe Lys Arg Ile Ile Ala Cys Ala Ser Tyr Lys
1400                1405                1410

Pro Ser Lys Glu Glu Ser Thr Ser Gly Ser Ser His Ala Val Met
1415                1420                1425

Asp Ile Ser Leu Pro Thr Gly Ile Gly Ala Asn Glu Glu Asp Leu
1430                1435                1440

Arg Ala Leu Val Glu Gly Val Asp Gln Leu Leu Thr Asp Tyr Gln
1445                1450                1455

Ile Lys Asp Gly His Val Ile Leu Gln Leu Asn Ser Ile Pro Ser
1460                1465                1470

Arg Asp Phe Leu Cys Val Arg Phe Arg Ile Phe Glu Leu Phe Gln
1475                1480                1485

Val Gly Phe Leu Asn Pro Ala Thr Phe Thr Val Tyr Glu Tyr His
1490                1495                1500
```

| | | | | | | | | | |
|---|---|---|---|---|---|---|---|---|---|
Arg Pro Asp Lys Gln Cys Thr Met Ile Tyr Ser Ile Ser Asp Thr
    1505                1510                1515

Arg Leu Gln Lys Val Cys Glu Gly Ala Ala Cys Thr Cys Val Glu
    1520                1525                1530

Ala Asp Cys Ala Gln Leu Gln Ala Glu Val Asp Leu Ala Ile Ser
    1535                1540                1545

Ala Asp Ser Arg Lys Glu Lys Ala Cys Lys Pro Glu Thr Ala Tyr
    1550                1555                1560

Ala Tyr Lys Val Arg Ile Thr Ser Ala Thr Glu Glu Asn Val Phe
    1565                1570                1575

Val Lys Tyr Thr Ala Thr Leu Leu Val Thr Tyr Lys Thr Gly Glu
    1580                1585                1590

Ala Ala Asp Glu Asn Ser Glu Val Thr Phe Ile Lys Lys Met Ser
    1595                1600                1605

Cys Thr Asn Ala Asn Leu Val Lys Gly Lys Gln Tyr Leu Ile Met
    1610                1615                1620

Gly Lys Glu Val Leu Gln Ile Lys His Asn Phe Ser Phe Lys Tyr
    1625                1630                1635

Ile Tyr Pro Leu Asp Ser Ser Thr Trp Ile Glu Tyr Trp Pro Thr
    1640                1645                1650

Asp Thr Thr Cys Pro Ser Cys Gln Ala Phe Val Glu Asn Leu Asn
    1655                1660                1665

Asn Phe Ala Glu Asp Leu Phe Leu Asn Ser Cys Glu
    1670                1675                1680

<210> SEQ ID NO 2
<211> LENGTH: 33
<212> TYPE: DNA
<213> ORGANISM: Artificial Sequence
<220> FEATURE:
<223> OTHER INFORMATION: primer

<400> SEQUENCE: 2
caattaaagc ttactataag aaggatttta caa                                33

<210> SEQ ID NO 3
<211> LENGTH: 33
<212> TYPE: DNA
<213> ORGANISM: Artificial Sequence
<220> FEATURE:
<223> OTHER INFORMATION: primer

<400> SEQUENCE: 3
caagttagat ctaagcacta gctactcaaa caa                                33

<210> SEQ ID NO 4
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 4
ctggaactgc atactttgaa attaaag                                      27

<210> SEQ ID NO 5
<211> LENGTH: 9
<212> TYPE: PRT
<213> ORGANISM: Artificial Sequence
<220> FEATURE:
<223> OTHER INFORMATION: Synthetic Polypeptide

```
<400> SEQUENCE: 5

Thr Gly Thr Ala Tyr Phe Glu Ile Lys
1               5

<210> SEQ ID NO 6
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 6
ctggaactgc actttga                                                    17

<210> SEQ ID NO 7
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 7

Thr Gly Thr Ala Leu
1               5
```